(12) United States Patent
Chou et al.

(10) Patent No.: US 11,701,158 B2
(45) Date of Patent: Jul. 18, 2023

(54) ABLATION SYSTEM WITH FORCE CONTROL

(71) Applicant: Acutus Medical, Inc., Carlsbad, CA (US)

(72) Inventors: Derrick Ren-Yu Chou, San Diego, CA (US); Marcus Frederick Julian, Vista, CA (US); Steven Anthony Yon, San Diego, CA (US); Randell L. Werneth, Eagle, ID (US); Alexander Higgins, San Diego, CA (US); Ricardo Roman, Chula Vista, CA (US); Alexander J. Asconeguy, Murrieta, CA (US); Christoph Scharf, Horgen (CH); Dennis O'Brien, Oceanside, CA (US); Rob Andre Pescar, San Diego, CA (US); Ahmad Falahatpisheh, San Marcos, CA (US); Tom Esbeck, Carlsbad, CA (US); Gerald M. Stobbs, III, Alpine, CA (US); Leo Mariappan, Oceanside, CA (US); Brandon Pratt Noheaikaika Lee, Vista, CA (US); James Calvin Allan, Boise, ID (US); Michael C. Oliveira, San Marcos, CA (US); Daniel Welsh, Encinitas, CA (US); R. Maxwell Flaherty, Topsfield, MA (US); J. Christopher Flaherty, Auburndale, FL (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 473 days.

(21) Appl. No.: 16/335,893

(22) PCT Filed: Oct. 11, 2017

(86) PCT No.: PCT/US2017/056064
§ 371 (c)(1),
(2) Date: Mar. 22, 2019

(87) PCT Pub. No.: WO2018/071490
PCT Pub. Date: Apr. 19, 2018

(65) Prior Publication Data
US 2020/0015876 A1    Jan. 16, 2020

Related U.S. Application Data

(60) Provisional application No. 62/504,139, filed on May 10, 2017, provisional application No. 62/406,748, filed on Oct. 11, 2016.

(51) Int. Cl.
*A61B 18/00* (2006.01)
*A61B 34/30* (2016.01)
(Continued)

(52) U.S. Cl.
CPC .............. *A61B 18/00* (2013.01); *A61B 18/06* (2013.01); *A61B 18/082* (2013.01);
(Continued)

(58) Field of Classification Search
CPC .............. A61B 18/00; A61B 2034/301; A61B 2090/065; A61B 2017/320069;
(Continued)

(56) References Cited

U.S. PATENT DOCUMENTS

| 5,951,471 A | 9/1999 | De La Rama et al. |
| 6,224,617 B1 | 5/2001 | Saadat et al. |

(Continued)

FOREIGN PATENT DOCUMENTS

| CN | 103747756 | 4/2014 |
| CN | 105358070 | 2/2016 |

(Continued)

OTHER PUBLICATIONS

Extended European Search Report dated Apr. 17, 2020 issued in corresponding European Application No. 17860322.1.
(Continued)

*Primary Examiner* — Aaron F Roane
(74) *Attorney, Agent, or Firm* — Onello & Mello, LLP

(57) ABSTRACT

An ablation system comprises: an ablation catheter and a console. The ablation catheter comprises: a shaft including
(Continued)

a proximal end, a distal portion and a distal end; an ablation element configured to deliver energy to tissue; and a force maintenance assembly comprising a force maintenance element and configured to control and/or assess contact force between the ablation element and cardiac tissue. The console is configured to operably attach to the ablation catheter and comprises: an energy delivery assembly configured to provide energy to the ablation element. Methods of ablating tissue are also provided.

18 Claims, 12 Drawing Sheets

(51) Int. Cl.
| | |
|---|---|
| *A61B 90/00* | (2016.01) |
| *A61B 17/32* | (2006.01) |
| *A61B 18/06* | (2006.01) |
| *A61B 18/08* | (2006.01) |
| *A61B 18/14* | (2006.01) |
| *A61B 18/24* | (2006.01) |
| *A61B 17/00* | (2006.01) |
| *A61B 18/02* | (2006.01) |
| *A61B 18/18* | (2006.01) |
| *A61M 25/01* | (2006.01) |

(52) U.S. Cl.
CPC .......... *A61B 18/1492* (2013.01); *A61B 18/24* (2013.01); *A61B 2017/00199* (2013.01); *A61B 2017/320069* (2017.08); *A61B 2018/00267* (2013.01); *A61B 2018/00291* (2013.01); *A61B 2018/00351* (2013.01); *A61B 2018/00577* (2013.01); *A61B 2018/00791* (2013.01); *A61B 2018/00839* (2013.01); *A61B 2018/00994* (2013.01); *A61B 2018/0212* (2013.01); *A61B 2018/1861* (2013.01); *A61B 2034/301* (2016.02); *A61B 2090/065* (2016.02); *A61M 25/0155* (2013.01); *A61M 25/0158* (2013.01); *A61M 2205/0216* (2013.01)

(58) Field of Classification Search
CPC ... A61B 18/06; A61B 18/082; A61B 18/1492; A61B 18/24; A61B 2017/00199; A61B 2018/00267; A61B 2018/00291; A61B 2018/00351; A61B 2018/00577; A61B 2018/00791; A61B 2018/00839; A61B 2018/00994; A61B 2018/0212; A61B 2018/1861; A61M 25/0155; A61M 25/0158; A61M 2205/0216
USPC .............................................................. 606/1
See application file for complete search history.

(56) References Cited

U.S. PATENT DOCUMENTS

| | | | |
|---|---|---|---|
| 8,021,361 B2 | 9/2011 | Paul et al. | |
| 8,114,122 B2 | 2/2012 | Nau, Jr. | |
| 8,540,659 B2 | 9/2013 | Berlin | |
| 8,852,228 B2 | 10/2014 | Nau, Jr. | |
| 9,492,228 B2 | 11/2016 | Lopes et al. | |
| 9,655,674 B2 | 5/2017 | Nau, Jr. | |
| 9,681,923 B2 | 6/2017 | Barley et al. | |
| 9,956,035 B2 | 5/2018 | Govari et al. | |
| 10,028,785 B2 | 7/2018 | Hu et al. | |
| 10,201,311 B2 | 2/2019 | Chou et al. | |
| 10,213,130 B2 | 2/2019 | Meredith | |
| 10,568,688 B2 | 2/2020 | Hu et al. | |
| 2007/0049821 A1* | 3/2007 | Willis .................. | A61B 8/0883 600/437 |
| 2007/0100332 A1 | 5/2007 | Paul et al. | |
| 2008/0108934 A1 | 5/2008 | Berlin | |
| 2009/0131930 A1 | 5/2009 | Gelbart et al. | |
| 2010/0179539 A1* | 7/2010 | Nau, Jr. ............. | A61B 18/1445 606/41 |
| 2012/0143185 A1 | 6/2012 | Nau, Jr. | |
| 2012/0165669 A1* | 6/2012 | Barley .................. | A61B 90/06 600/439 |
| 2013/0066304 A1* | 3/2013 | Belson .................. | A61B 17/00 606/1 |
| 2013/0103064 A1 | 4/2013 | Arenson et al. | |
| 2013/0178851 A1 | 7/2013 | Lopes et al. | |
| 2014/0018665 A1 | 1/2014 | Meredith | |
| 2014/0236208 A1* | 8/2014 | Cahill .............. | A61B 17/32053 606/185 |
| 2015/0018827 A1 | 1/2015 | Nau, Jr. | |
| 2015/0272667 A1 | 10/2015 | Govari et al. | |
| 2015/0366508 A1 | 12/2015 | Chou et al. | |
| 2016/0008058 A1 | 1/2016 | Hu et al. | |
| 2016/0317843 A9 | 11/2016 | Arenson et al. | |
| 2018/0360536 A1 | 12/2018 | Hu et al. | |
| 2019/0159729 A1 | 5/2019 | Chou et al. | |
| 2020/0383723 A1 | 12/2020 | Hu et al. | |

FOREIGN PATENT DOCUMENTS

| | | |
|---|---|---|
| CN | 105934212 | 9/2016 |
| JP | 2010162349 | 7/2010 |
| JP | 2013504398 | 2/2013 |

OTHER PUBLICATIONS

Chinese Office Action dated Jul. 1, 2021 issued in corresponding Chinese Application No. 201780074701.1.
Chinese Search Report dated Jun. 27, 2021 issued in corresponding Chinese Application No. 201780074701.1.
International Search Report and Written Opinion dated Dec. 12, 2017 issued in corresponding International Application No. PCT/US2017/056064.
Japanese Office Action dated Jul. 27, 2021 issued in corresponding Japanese Application No. 2019-519643, with machine translation to English.
European Office Action dated Dec. 7, 2022 issued in corresponding European Application No. 17860322.1.

* cited by examiner

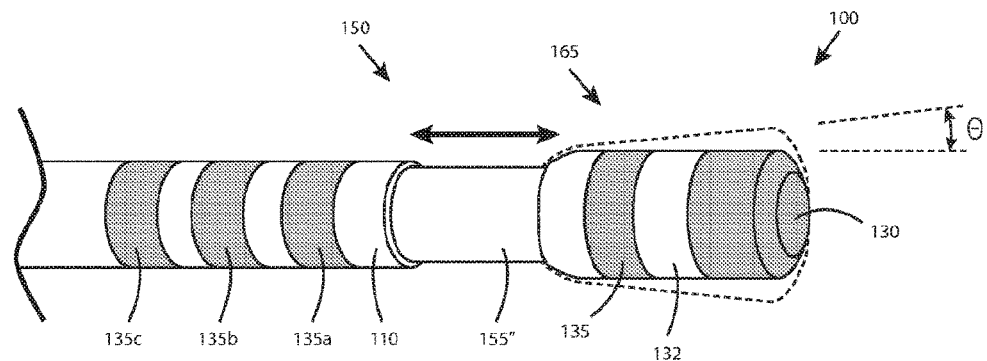
FIG 8
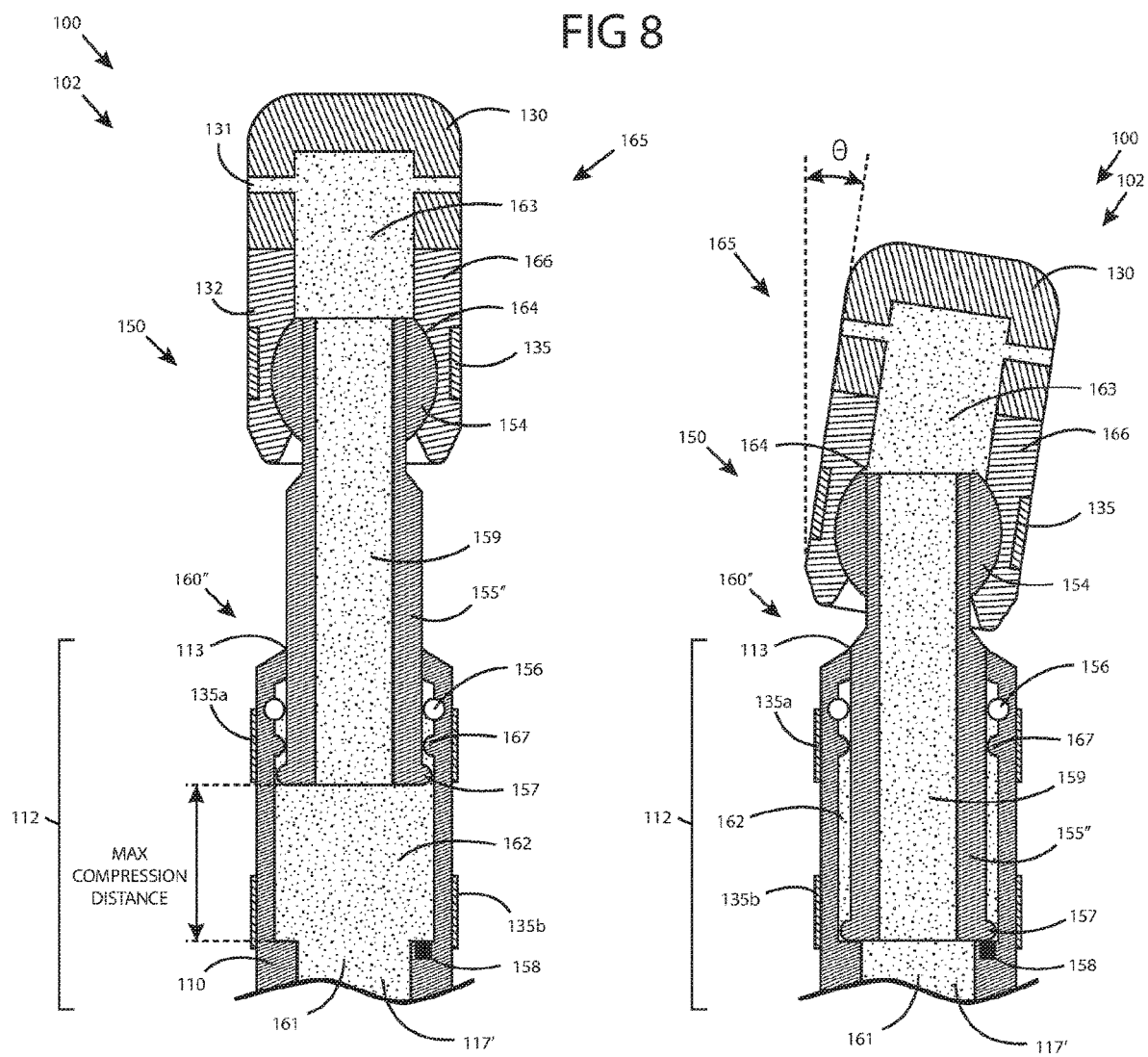
FIG 8A
FIG 8B

ABLATION SYSTEM WITH FORCE CONTROL

RELATED APPLICATIONS

The present application claims priority under 35 USC 119(e) to U.S. Provisional Application Ser. No. 62/406,748, entitled "Ablation System with Force Control", filed Oct. 11, 2016, and U.S. Provisional Application Ser. No. 62/504,139, entitled "Ablation System with Force Control", filed May 10, 2017, each of which is hereby incorporated by reference in its entirety for all purposes.

The present application, while not claiming priority to, may be related to U.S. application Ser. No. 14/003,671, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517, which claimed priority to U.S. Patent Provisional Application Ser. No. 61/451,357, each of which is hereby incorporated by reference in its entirety for all purposes.

The present application, while not claiming priority to, may be related to U.S. application Ser. No. 14/422,941, entitled "Catheter, System and Methods of Medical Uses of Same, Including Diagnostic and Treatment Uses for the Heart", filed Feb. 20, 2015, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, published as WO 2014/036439, which claims priority to U.S. Patent Provisional Application Ser. No. 61/695,535, entitled "System and Method for Diagnosing and Treating Heart Tissue", filed Aug. 31, 2012, which is hereby incorporated by reference in its entirety for all purposes.

The present application, while not claiming priority to, may be related to U.S. application Ser. No. 14/762,944, entitled "Expandable Catheter Assembly with Flexible Printed Circuit Board (PCB) Electrical Pathways", filed Jul. 23, 2015, which is a 35 USC 371 national stage filing of Patent Cooperation Treaty Application No. PCT/US2014/015261, entitled "Expandable Catheter Assembly with Flexible Printed Circuit Board (PCB) Electrical Pathways", filed Feb. 7, 2014, published as WO 2014/124231, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference in its entirety for all purposes.

The present application, while not claiming priority to, may be related to Patent Cooperation Treaty Application No. PCT/US2016/032420, entitled "Localization System and Method Useful in the Acquisition and Analysis of Cardiac Information", filed May 13, 2016, which claims priority to U.S. Patent Provisional Application Ser. No. 62/161,213, entitled "Localization System and Method Useful in the Acquisition and Analysis of Cardiac Information", filed May 13, 2015, which is hereby incorporated by reference in its entirety for all purposes.

FIELD OF THE INVENTION

The present invention relates generally to ablation systems, catheters and methods, particularly those that maintain and/or monitor force between ablation elements and tissue.

BACKGROUND OF THE INVENTION

Tissue ablation is used to treat numerous patient diseases and disorders, such as cardiac arrhythmias and tumor treatments. Tissue ablation can be performed with devices that deliver various forms of energy, such as radio frequency (RF) energy; cryoablation energy; sound energy such as ultrasound energy, laser energy, microwave energy, and the like. Success of the tissue ablation procedure often depends on sufficient, but not excessive force being maintained between the ablation device and the tissue to be ablated. There is a need for improved ablation systems that control and/or monitor the force applied to tissue by an ablation device that delivers energy to the tissue.

SUMMARY

Embodiments of the systems, devices and methods described herein can be directed to systems, devices and methods for delivering energy to tissue, such as to ablate tissue. The systems and devices can be configured to control and/or monitor force applied to tissue by one or more ablation elements of the system. The systems and devices can be used in cardiac ablation procedures, such as to treat an arrhythmia, a nerve ablation procedure, and/or a tumor removal procedure.

According to one aspect of the inventive concept, provided is an ablation system comprising an ablation catheter, which includes a shaft including a proximal end, a distal portion and a distal end; an ablation element configured to deliver energy to tissue; and a force maintenance assembly comprising a force maintenance element and configured to control and/or assess contact force between the ablation element and cardiac tissue. The ablation system also includes a console configured to operably attach to the ablation catheter and comprising an energy delivery assembly configured to provide energy to the ablation element.

In some embodiments, the ablation catheter further comprises a contact sensor configured to produce a signal representative of the amount of contact between the ablation element and tissue.

In some embodiments, the ablation system is configured to determine whether the ablation element is in contact with the cardiac tissue, based, at least in part, on the signal from the contact sensor.

In some embodiments, the ablation system is configured to differentiate sufficient contact versus insufficient contact for ablation, based, at least in part, on the signal from the contact sensor, wherein sufficient contact and insufficient contact is determined based on a threshold contact level.

In some embodiments, the ablation system is configured to determine a quantified contact amount from among a range of contact values, based, at least in part, on the signal from the contact sensor.

In some embodiments, the signal comprises a voltage signal.

In some embodiments, the voltage signal has a resolution indicating a measurable change in proximity and/or orientation of the ablation element with respect to the cardiac tissue.

In some embodiments, the resolution is at least 0.015 mV per 0.1 mm change in distance between the sensing element and the cardiac surface.

In some embodiments, the resolution is at least 0.010 mV per 0.1 mm change in distance between the sensing element and the cardiac surface.

In some embodiments, the system is configured to detect a surface and/or an object within at least 12 mm of one or more sensing element based at least one part on the voltage signal.

In some embodiments, the system is configured to detect a surface and/or an object within at least 10 mm of one or more sensing element based at least one part on the voltage signal.

In some embodiments, the system is configured to detect a surface and/or an object within at least 12 mm of one or more sensing element based at least one part on the voltage signal.

In some embodiments, the contact sensor is chosen from a group consisting of a piezoelectric strain sensor, a piezoelectric acoustic sensor, an impedance contact sensor, an electrode contact sensor, a pressure contact sensor, or an optical sensor.

In some embodiments, the contact sensor is or includes at least one piezoelectric strain sensor that is configured to generate a charge when under a compressive load.

In some embodiments, the at least one piezoelectric strain sensor is a plurality of piezoelectric strain sensors and wherein the system is configured to compare voltages from the plurality of piezoelectric strain sensors to determine an angular orientation of the ablation element with respect to the catheter shaft.

In some embodiments, the contact sensor is or includes at least one impedance contact sensor configured to measure impedance, wherein a decrease in impedance indicates tissue contact.

In some embodiments, the contact sensor is or includes a plurality of electrodes, wherein a change in a signal among or between electrodes indicates tissue contact and/or a mechanical stimulus applied to the force maintenance assembly.

In some embodiments, the contact sensor is or includes at least one electrode contact sensor comprising a pair of electrodes, wherein a change in a signal between electrodes in the pair of electrodes indicates tissue contact and/or a mechanical stimulus applied to the force maintenance assembly.

In some embodiments, the console is configured to monitor the pair of electrodes for signal changes.

In some embodiments, the console is configured to determine proximity of the ablation element to the cardiac tissue based on the signal changes.

In some embodiments, the console is configured to determine if there is contact of the ablation element with the cardiac tissue based on the signal changes.

In some embodiments, the console is configured to determine an angle of attack of the ablation element with respect to the cardiac tissue based on the signal changes.

In some embodiments, the system is configured to inject a signal through the catheter to enable contact sensing using the pair of electrodes.

In some embodiments, the system is configured to transmit a signal from a first (source) electrode and receive the signal by a second (sink) electrode, wherein the signal is used by the console to determine a proximity and/or an orientation of the ablation catheter to an object, surface, and/or boundary within the cardiac chamber.

In some embodiments, the signal comprises an applied voltage and/or a sourced current, such as a voltage or current having a frequency between 1 kHz and 1 MHz.

In some embodiments, the signal comprises an applied voltage and/or a sourced current, such as a voltage or current having a frequency between 10 kHz and 100 kHz.

In some embodiments, the signal comprises an applied voltage and/or a sourced current, such as a voltage or current having a frequency of or about 20 kHz.

In some embodiments, the signal creates an electrical field between the first (source) electrode and the second (sink) electrode, wherein the electrical field is measured by one or more additional sensors of system, such as by one or more electrodes of the ablation catheter, wherein a spatial distribution of current flow through blood or tissue surrounding the source and sink electrodes establishes a spatially-varying potential field that can be measured at the location of any electrodes on the ablation catheter or other device within the potential field as a voltage relative to a reference electrode, such as a reference patch electrode.

In some embodiments, the console is configured to determine or measure a spacing between any two or more electrodes within the potential field to determine a compression distance of an element of the force maintenance assembly.

In some embodiments, the console is configured to process a change in spacing as a function of time to determine a stability of engagement of the force maintenance assembly, which can correlate to the stability of tissue contact.

In some embodiments, the console is configured to determine a shape and/or a spatial structure of the potential field by boundary conditions established by the cardiac tissue or other variations in impedance in the local environment.

In some embodiments, the console is configured to derive the shape and/or the spatial structure of the field from measurements at any electrode on the ablation catheter or any other device within the potential field using an algorithm such as a fitting function.

In some embodiments, a spatial distribution of current flow varies as a function of a proximity and/or an orientation of structures and/or boundaries of differing characteristic impedances near the source and the sink electrodes.

In some embodiments, the console is configured to select different electrodes as the source and sink electrodes, as alternated, modulated and/or otherwise multiplexed different pairs of electrodes on the ablation catheter, to obtain alternate measures of the effect that the boundary conditions of the local environment have on the shape and spatial structure of the field.

In some embodiments, when current is sourced and/or sinked from an alternate pair of electrodes, an alternate potential field is established and alternate measurements from any electrodes within the alternate potential field are measured by the console.

In some embodiments, if one or more alternate field configurations are established and measured in a duration of time short enough that the local environment, in terms of relative position and/or orientation of boundary conditions, remains the same or about the same for a duration of time, the console is configured to use the set of multiplexed, alternate measurements to establish a system of equations for which an algorithm can be used to determine and/or reconstruct the state of the boundary conditions for the duration of time to determine the proximity and the orientation of the ablation catheter with respect to the cardiac tissue.

In some embodiments, the duration of time is less than 1 second, less than 100 ms, and/or less than 10 ms.

In some embodiments, the at least 3 electrodes are used by the console to determine the boundary conditions, such as at least 4 or at least 5 electrodes, to support alternate source/ sink electrode configuration having at least 1 source/sink electrode pair, at least 2 source/sink electrode pairs, at least 6 source/sink electrode pairs, and/or at least 10 alternate source/sink electrode pairs, to determine a complexity of the boundary conditions.

In some embodiments, the contact sensor is or includes at least one pressure contact sensor configured to measure irrigation flow to determine tissue contact, wherein blocked irrigation channels within the shaft causes sensed pressure to rise indicating contact.

In some embodiments, the ablation catheter further comprises a handle positioned on the proximal end of the shaft.

In some embodiments, the flow sensor is an ultrasonic flow sensor or other flow sensor.

In some embodiments, the contact sensor further comprises a pressure sensor, wherein blocked irrigation channels within the shaft causes sensed pressure to rise indicating contact.

In some embodiments, the handle comprises at least one control.

In some embodiments, the handle is configured to communicate with the force maintenance assembly.

In some embodiments, the at least one control comprises one or more buttons, switches, and/or levers.

In some embodiments, the handle is configured to mechanically, electro-mechanically, and/or electrically control the force maintenance assembly.

In some embodiments, the ablation catheter further comprises at least one mapping electrode.

In some embodiments, the force maintenance assembly is positioned in the handle.

In some embodiments, the catheter includes one or more wires running between the force maintenance assembly and the handle through the shaft and the one or more wires are coiled to minimize resistance when the force maintenance assembly is compressed.

In some embodiments, the force maintenance assembly comprises a plurality of compression areas from the handle to the ablation element.

In some embodiments, the plurality of compression areas includes one or more hydraulic, spring, and/or magnetic force maintenance elements.

In some embodiments, the ablation catheter further comprises at least one conduit having disposed therein one or more wire or conductive trace, optical fiber, fluid delivery tube, and/or wave guide, and/or mechanical linkage, each of which is configured to operably couple one or more components of the console to one or more components of ablation catheter.

In some embodiments, the fluid delivery tube comprises at least one hydraulic fluid tube, pneumatic fluid tube, and/or fluid irrigation tube.

In some embodiments, the mechanical linkage includes at least one translating filament.

In some embodiments, the at least one mapping electrode comprises a ring electrode.

In some embodiments, the at least one mapping electrode is positioned on the shaft distal portion.

In some embodiments, the at least one mapping electrode is positioned on the ablation catheter distal portion.

In some embodiments, the at least one mapping electrode comprises a mapping electrode positioned a fixed distance from the ablation element.

In some embodiments, the force maintenance assembly comprises a translatable portion, and wherein the ablation element and the mapping electrode are positioned on the translatable portion.

In some embodiments, the ablation element comprises an electrode, and wherein the system is configured to gather bipolar biopotential data between the ablation element and the mapping electrode.

In some embodiments, the ablation catheter further comprises an irrigation lumen configured to deliver fluid to tissue proximate the ablation element.

In some embodiments, the irrigation lumen exits at a location proximal to the ablation element.

In some embodiments, the ablation element comprises at least one hole through which the irrigation lumen exits.

In some embodiments, the system further comprises fluid for delivery through the irrigation lumen.

In some embodiments, the fluid is configured to lubricate the force maintenance assembly.

In some embodiments, the fluid is configured to cool the ablation element and/or tissue.

In some embodiments, the ablation catheter further comprises an articulating tip assembly.

In some embodiments, the articulating tip assembly comprises a spherical member and a cavity that rotatably engages the spherical member.

In some embodiments, the force maintenance assembly comprises a floating tip portion at the catheter distal end, and wherein the ablation element is positioned on the force maintenance assembly floating tip portion.

In some embodiments, the ablation element is positioned on the distal portion of the shaft.

In some embodiments, the ablation element has a length of approximately 3.5 mm, such as a length between 3.0 mm and 4.0 mm.

In some embodiments, the ablation element comprises at least one electrode.

In some embodiments, the at least one electrode comprises a gold and/or a platinum iridium electrode.

In some embodiments, the ablation element is configured to deliver radio frequency (RF) energy to tissue.

In some embodiments, the ablation element is configured to deliver energy to tissue.

In some embodiments, the ablation element is configured to deliver energy to tissue in a form selected from the group consisting of: thermal energy; heat energy; cryogenic energy; electromagnetic energy; radio frequency (RF) energy; microwave energy; light energy; light energy provided by a laser; sound energy; subsonic energy; ultrasound energy; chemical energy; and combinations thereof.

In some embodiments, the ablation catheter is configured to deliver at least two forms of energy selected from the group consisting of: electromagnetic energy; RF energy; microwave energy; light energy; laser light energy; cryogenic energy; ultrasound energy; and combinations thereof.

In some embodiments, the ablation element includes at least one electrode, at least one optical element configured to deliver light energy, and/or at least one cryogenic fluid delivery element positioned on the distal end of ablation catheter in a "tip electrode" configuration.

In some embodiments, the ablation element comprises two, three, or more ablation elements, such as multiple electrodes configured to deliver monopolar and/or bipolar electromagnetic ablation energy to ablate tissue.

In some embodiments, the force maintenance assembly is positioned in the shaft.

In some embodiments, the force maintenance assembly is positioned on the distal end of the shaft.

In some embodiments, the force maintenance assembly is axially aligned with a portion of the shaft.

In some embodiments, the force maintenance assembly is axially aligned with a distal portion of the shaft.

In some embodiments, the force maintenance assembly is configured to absorb mechanical shock.

In some embodiments, the force maintenance assembly is configured to dynamically respond to movement of the heart wall.

In some embodiments, the force maintenance assembly is configured to compress up to a max compression distance, and wherein the max compression distance comprises a length between 0.1 mm and 10 mm.

In some embodiments, the force maintenance assembly is configured to compress up to a max compression distance between 0.1 mm and 5 mm.

In some embodiments, the force maintenance assembly is configured to compress over a travel distance, and wherein the force maintenance assembly is further configured to provide a pre-determined force over the travel distance.

In some embodiments, the force maintenance assembly is configured to provide a constant force over the travel distance.

In some embodiments, the force maintenance assembly is configured to provide a force that varies over the travel distance.

In some embodiments, the force maintenance assembly is configured to provide a force that varies within a pre-determined range over the travel distance.

In some embodiments, the force maintenance assembly is configured to provide a force between 5 gmf and 30 gmf over the travel distance.

In some embodiments, the force maintenance assembly is configured to provide a force between 10 gmf and 30 gmf over the travel distance.

In some embodiments, the ablation catheter comprises a first ablation catheter as described above and the system comprises a second ablation catheter comprising: a second shaft including a proximal end, a distal portion and a distal end; a second ablation element configured to deliver energy to tissue; and a second force maintenance assembly comprising a second force maintenance element and configured to control and/or assess contact force between the second ablation element and cardiac tissue. The first ablation catheter is configured for use in an atria of the heart. The second ablation catheter is configured for use in a ventricle of the heart. And the first ablation catheter force maintenance assembly comprises a shorter max compression distance than the max compression distance of the second ablation catheter second force maintenance assembly max compression distance.

In some embodiments, the second catheter second force maintenance assembly max compression distance is at least 1 mm longer than the first catheter force maintenance assembly max compression distance.

In some embodiments, the ablation catheter is configured to treat an atria of the heart, and wherein the force maintenance assembly is configured to provide a max compression distance selected from the group consisting of: a distance less than 10 mm; a distance less than 5 mm; a distance less than or equal to 3 mm; a distance of between 2 mm and 3 mm; and combinations thereof.

In some embodiments, the ablation catheter is configured to treat a ventricle of the heart, and wherein the force maintenance assembly is configured to provide a max compression distance of between 4 mm and 6 mm.

In some embodiments, the ablation system further comprises a locking element configured to lock the force maintenance assembly to prevent linear and/or angular movement of the ablation element with respect to the shaft.

In some embodiments, the force maintenance assembly further comprises at least one displacement sensor configured to produce a signal correlating to a travel distance of the force maintenance assembly.

In some embodiments, the system is configured to determine when the travel distance is equal to the max compression distance based on the sensor signal.

In some embodiments, the displacement sensor is a capacitive sensor, wherein a change in capacitance correlates to the displacement.

In some embodiments, the displacement sensor is an inductive spring sensor, optionally configured to use synchronous demodulation to determine displacement, wherein a change in inductance correlates to the displacement.

In some embodiments, the displacement sensor is a linear variable differential transformer (LVDT).

In some embodiments, the system is configured to continue to provide energy to the ablation element when the travel distance reaches the maximum compression distance.

In some embodiments, the system is configured to limit the providing of energy to the ablation element, when the travel distance reaches the maximum compression distance.

In some embodiments, the system is configured to stop the providing of energy to the ablation element, when the travel distance reaches the maximum compression distance.

In some embodiments, the ablation system further comprises at least one displacement sensor configured to determine a linear and/or angular displacement, with respect to the shaft, of a floating tip portion of the ablation catheter comprising the ablation element.

In some embodiments, the at least one displacement sensor is selected from a group consisting of: a capacitive sensor, a tactile sensor, a linear potentiometer, a (linear variable differential transformer) LVDT sensor, a Hall effect sensor, an optical sensor, a load cell, and an indicative sensor.

In some embodiments, the at least one displacement sensor is or includes a capacitive sensor, wherein displacement of the floating tip portion causes changes in capacitance sensed by capacitive elements of the capacitive sensor that are proportional to changes in distance of the floating tip portion.

In some embodiments, the force maintenance assembly includes a bellows surrounding the capacitive sensor and the bellows is configured as a shock absorber.

In some embodiments, the console is configured to calculate a force applied to the force maintenance assembly from a spring force of the bellows and a displacement measured by the capacitive sensor.

In some embodiments, the at least one displacement sensor is or includes a linear displacement sensor, wherein electromagnetic coupling is used between stationary sensor elements on the shaft and movable sensor elements on the floating tip portion to determine linear displacement.

In some embodiments, the at least one displacement sensor is or includes a LVDT sensor configured to measure linear displacement of the floating tip portion with respect to the catheter shaft.

In some embodiments, the force maintenance assembly includes a bellows surrounding the LVDT sensor and the bellows is configured as a shock absorber.

In some embodiments, the console is configured to calculate a force applied to the force maintenance assembly from a spring force of the bellows and a displacement measured by the LVDT sensor.

In some embodiments, the at least one displacement sensor is or includes a tactile sensor, wherein displacement of the floating tip portion causes contact with a tactile sensor within the catheter shaft.

In some embodiments, the at least one displacement sensor is or includes an optical sensor, wherein the shaft includes a light source and a light sensor and the floating tip portion includes a movable element having a light blocking element configured to at least partially obstruct light from the light source from passing to the light sensor when the force maintenance assembly is compressed.

In some embodiments, the light blocking element includes a tapered slit opening that increasingly obstructs light from the light source as the force maintenance assembly is increasingly compressed.

In some embodiments, the at least one displacement sensor is or includes a load cell, wherein the load cell is attached to the floating tip portion.

In some embodiments, the at least one displacement sensor is or includes one or more inductive sensor.

In some embodiments, the inductive sensor is configured to determine one or more of linear displacement, angular displacement, overall position, and/or orientation of a movable portion of the force maintenance assembly.

In some embodiments, the inductive sensor comprises one or more coils distributed within the force maintenance assembly.

In some embodiments, the force maintenance assembly includes a plunger movable within the catheter shaft and the inductive sensor includes a magnetic material forming part of or coupled to the plunger and forming part of or coupled to the catheter shaft.

In some embodiments, the magnetic material includes one or more ferrite strips forming part of or coupled to the plunger and/or one or more ferrite strips forming part of or coupled to the catheter shaft.

In some embodiments, the one or more ferrite strips forming part of or coupled to the plunger comprises ferrite tape wrapped around a portion of the plunger and the one or more ferrite strips forming part of or coupled to the catheter shaft comprises ferrite tape wrapped around a portion of the catheter shaft.

In some embodiments, the magnetic material comprises a mu-metal or other ferrous material.

In some embodiments, the movement of the plunger within the shaft changes a self-inductance of the inductive sensors.

In some embodiments, the changes in the self-inductance of the inductive sensors occurs in a stepped or step-like manner.

In some embodiments, the inductive sensor includes at least three coils configured to detect lateral components of a force applied to the force maintenance assembly.

In some embodiments, the inductive sensor includes at least one coil at the distal end of the catheter shaft configured to measure axial components of a force applied to the force maintenance assembly.

In some embodiments, a stiffness and a position of a floating tip portion of the force maintenance assembly is configured to be electromagnetically tuned in response to a feedback signal induced by compression and expansion of the force maintenance assembly.

In some embodiments, the inductive sensor is configured to measure a resonant frequency change using IQ demodulation to determine contact of the ablation element with the cardiac tissue.

In some embodiments, the at least one displacement sensor includes a displacement sensor in a handle positioned on the proximal end of the shaft.

In some embodiments, the at least one displacement sensor includes a displacement sensor in the proximal end of the shaft.

In some embodiments, the at least one displacement sensor includes a displacement sensor in the distal end of the shaft.

In some embodiments, the at least one displacement sensor includes one or more displacement sensor in the shaft between the proximal and distal ends of the shaft.

In some embodiments, the system comprises hydraulic fluid, and wherein the force maintenance element comprises a hydraulic piston into which the hydraulic fluid is delivered.

In some embodiments, the system is configured to further deliver the hydraulic fluid to the cardiac tissue.

In some embodiments, the hydraulic piston comprises a chamber and an exterior surface, and wherein the system is configured to deliver the hydraulic fluid to the chamber of the hydraulic piston and to the exterior surface of the hydraulic piston.

In some embodiments, the console is configured to deliver the hydraulic fluid to the hydraulic piston.

In some embodiments, the console comprises a fluid delivery device configured to deliver the hydraulic fluid.

In some embodiments, the fluid delivery device is configured to deliver the hydraulic fluid to the cardiac tissue under control of the console.

In some embodiments, the fluid delivery device comprises a device selected from the group consisting of: peristaltic pump; syringe pump; gravity-feed flow controller; and combinations thereof.

In some embodiments, the fluid delivery device comprises a pump, and the system further comprises an accumulator located downstream of the pump configured to reduce and/or minimize a pulsatile nature of the pump.

In some embodiments, the hydraulic fluid comprises saline.

In some embodiments, the force maintenance element comprises a spring element or a spring material.

In some embodiments, the spring element comprises a constant force spring.

In some embodiments, the constant force spring material comprises one or more materials selected from the group consisting of: Nitinol and/or other shaped memory metal; a super elastic polymer; a polymer; and combinations thereof.

In some embodiments, the polymer or the super-elastic polymer comprises polymers of varying durometers arranged in parallel and/or in series within the catheter shaft.

In some embodiments, the spring element has a shape that minimizes outer diameter growth when compressed.

In some embodiments, the spring element is configured to provide a force range with a maximum force from a plurality of different angles.

In some embodiments, the console is configured to apply heating, cooling and/or an electric current to the spring material to adjust forces of the spring element.

In some embodiments, the spring element comprises a metal shaft, piston or other tube with one or more laser cuts that configure the tube as a spring.

In some embodiments, a spring constant of spring element is chosen to enable compression of the spring element in response to a force experienced by a floating tip portion of the ablation catheter that does not compromise or damage the tissue against which the ablation element is in contact.

In some embodiments, the spring element comprises resiliently biased bellows.

In some embodiments, the force maintenance assembly further comprises a piston, and wherein the spring engages the piston.

In some embodiments, the shaft slidingly engages the piston.

In some embodiments, the piston comprises a flange that engages the shaft and limits translation of the piston distally.

In some embodiments, the piston comprises a lumen.

In some embodiments, the force maintenance assembly further comprises a deflection sensor.

In some embodiments, the ablation catheter includes a floating tip portion comprising the ablation element, and the deflection sensor is configured to measure an angle and/or magnitude of deflection of the floating tip portion with respect to a known axis of the shaft.

In some embodiments, the console further comprises a force maintenance module.

In some embodiments, the force maintenance module is configured to adjust the force maintenance assembly.

In some embodiments, the force maintenance module is configured to provide a control signal to the force maintenance assembly.

In some embodiments, the force maintenance assembly comprises a hydraulic piston, and wherein the force maintenance assembly controls a parameter selected from the group consisting of: fluid flow to the hydraulic piston; fluid pressure within the hydraulic piston; and combinations thereof.

In some embodiments, the console further comprises a processor configured to perform one or more mathematical operations on one or more received signals, and to produce a result correlating to a quantitative or qualitative measure of a force applied by ablation catheter to tissue, an amount of compression of the force maintenance assembly, an orientation of the ablation catheter, a proximity of a portion of the ablation catheter to the cardiac tissue, and/or a level or quality of contact between a portion of the ablation catheter and the cardiac tissue.

In some embodiments, the one or more mathematical operations comprises an operation or function selected from the group consisting of: arithmetic operations; statistical operations; linear and/or non-linear functions; operations as a function of time; operations as a function of space or distance; a comparison to a threshold; a comparison to a range; and combinations of one or more of these.

In some embodiments, the console is configured to adjust the force maintenance assembly.

In some embodiments, the catheter further comprises a sensor configured to provide a signal to the console.

In some embodiments, the sensor signal correlates to the travel distance of the force maintenance assembly.

In some embodiments, the console disables delivery of energy to the ablation element when the travel distance reaches the max compression distance.

In some embodiments, the console comprises a manual override configured to allow delivery of energy to the ablation element when the travel distance reaches the max compression distance.

In some embodiments, the console generates a notification for output to a clinician when the travel distance reaches the maximum compression distance.

In some embodiments, the system is configured to allow continued energy delivery to the ablation element when the travel distance reaches the maximum compression distance.

In some embodiments, the console generates a notification for output to a clinician when the travel distance is below a minimum distance.

In some embodiments, the sensor signal correlates to the force applied to the cardiac tissue by the ablation element.

In some embodiments, the system is configured to detect if the force is below a threshold.

In some embodiments, the system is configured to detect if the force is below a threshold selected from the group consisting of: 1 gmf; 3 gmf; 5 gmf; 7 gmf; 10 gmf and combinations thereof.

In some embodiments, the system is configured to provide an alert if the force falls below the threshold.

In some embodiments, the system is configured to prevent delivery of energy by the ablation element if the force falls below the threshold.

In some embodiments, the console disables delivery of energy to the ablation element when contact between the ablation element and tissue is below a threshold.

In some embodiments, the console comprises a manual override configured to allow delivery of energy to the ablation element when contact between the ablation element and tissue is below the threshold.

In some embodiments, the console further comprises a user interface.

In some embodiments, the user interface comprises a user input component selected from the group consisting of: joystick; keyboard; mouse; touchscreen; and combinations thereof.

In some embodiments, the user interface comprises a display.

In some embodiments, the system is configured to provide information on the display representing a level of contact between the ablation element and tissue.

In some embodiments, the provided information comprises information selected from the group consisting of: sufficient contact achieved; insufficient contact achieved; level of force achieved; level of pressure achieved; distance or proximity to a boundary; orientation or angle-of-attack to a boundary; topology of a proximate boundary; contact efficiency; and combinations thereof.

In some embodiments, the energy delivery module comprises a radio frequency (RF) generator that provides the energy to the ablation element.

In some embodiments, the energy delivery module comprises a device selected from the group consisting of: RF generator; light energy delivery unit (e.g. a laser light energy delivery unit); cryogenic energy delivery unit; ultrasound energy delivery unit; and combinations thereof.

In some embodiments, the system further comprises at least one functional element.

In some embodiments, the at least one functional element comprises one or more transducers selected from the group consisting of: heating element; cooling element; vibrational transducer; ultrasound transducer; electrode; light delivery element; drug or other agent delivery element; and combinations thereof.

In some embodiments, the at least one functional element comprises one or more sensors selected from the group consisting of: a physiologic sensor; a blood pressure sensor; a blood gas sensor; a pressure sensor; a strain gauge; a force sensor; a chemical sensor; an impedance sensor; a magnetic sensor; an electrode; a displacement sensor; and combinations thereof.

In some embodiments, the at least one functional element includes one or more functional element configured to provide feedback and/or an alert to the console indicating a status of one or more components of the ablation system.

In some embodiments, the one or more functional element comprises an element selected from the group consisting of: a haptic transducer; a light source, such as an LED light source; an audio transducer, such as a speaker; and combinations of one or more thereof.

In some embodiments, the functional element comprises a haptic transducer configured to generate at least one output to the console that indicates a status of one or more components of system.

In some embodiments, the at least one output of the haptic transducer includes a haptic signal that varies to indicate one or more characteristics selected from the group consisting of: frequency of the haptic signal; pulse width of the haptic signal; intensity of the haptic signal; pattern of the haptic signal, such as a Morse code pattern or other code pattern; and combinations of one or more of these.

In some embodiments, the functional element comprises a light source, and the housing of the handle comprises an at least partially translucent housing portion, such that the console causes the light source to illuminate the housing portion to indicate an alert and/or a state of system.

In some embodiments, the console is configured to adjust an intensity of the light to correspond with one or more variable conditions, such as the proximity of ablation element to tissue, amount of compression of force maintenance assembly, level of pressure exerted by catheter on the cardiac tissue, and combinations of one or more of these.

In some embodiments, the console is configured to vary a color of the light to represent different alerts and/or system information.

In some embodiments, the console is configured to modulate or pattern the light to indicate any one or more alerts and/or states of system.

In some embodiments, the alert and/or state indicates insufficient energy delivery and/or insufficient contact with the cardiac tissue.

In some embodiments, the ablation system further comprises a mapping catheter.

In some embodiments, the mapping catheter comprises an expandable assembly comprising multiple electrodes.

In some embodiments, the expandable assembly further comprises multiple ultrasound transducers.

In some embodiments, the mapping catheter further comprises at least one functional element.

In some embodiments, the console further comprises a mapping module configured to operably interface with the mapping catheter.

In some embodiments, the mapping module comprises an ultrasound module configured to record and/or process ultrasound information.

In some embodiments, the mapping module comprises a biopotential module configured to record and/or process biopotential information.

In some embodiments, the ablation system further comprises at least one patient patch.

In some embodiments, the at least one patient patch is configured to transmit and/or receive electrical signals through and/or from the patient.

In some embodiments, the force maintenance assembly comprises a plurality of compression areas from the handle to the ablation element.

In some embodiments, the plurality of compression areas includes one or more hydraulic, spring, and/or magnetic force maintenance elements.

In some embodiments, the force maintenance element comprises a hook or a barb configured to selectively pierce the cardiac tissue.

In some embodiments, the force maintenance element comprises a vacuum configured to selectively apply suction to the cardiac tissue to control or maintain contact with the ablation element.

In some embodiments, the force maintenance element comprises a cryogenic element configured to cryogenically stick to the cardiac tissue.

In some embodiments, the ablation element is a cryogenic ablation element configured to cryogenically stick to the cardiac tissue.

In some embodiments, the force maintenance assembly comprises at least one pair of magnets positioned with opposing polarities directed toward each other so that the magnets repel each other to generate a spring force.

In some embodiments, the at least one pair of magnets generates a constant spring force.

In some embodiments, a floating tip portion of the ablation catheter comprises the ablation element and is coupled to the shaft by the force maintenance assembly, and the at least one pair of magnets is oriented to bias the floating tip portion in a straight orientation relative to the shaft.

In some embodiments, the ablation system further comprises a bellows surrounding at least a portion of the force maintenance element.

In some embodiments, the bellows forms a part of the force maintenance assembly and provides a spring force.

In some embodiments, the bellows is configured to shield the force maintenance element from in-flow of biological material.

In some embodiments, the bellows is formed of a thin-walled elastomer, TPU, or TPV to avoid adding stiffness to the force maintenance assembly.

In some embodiments, the bellows is formed of a pre-stretched silicon extrusion, which is configured not to bunch when compressed.

In some embodiments, the force maintenance assembly is configured to maintain the ablation element in contact with the cardiac tissue from a fully compressed state to a fully uncompressed state during oscillations of the cardiac tissue, wherein the oscillation includes reciprocating motions of the cardiac tissue.

In some embodiments, the oscillations have a frequency of at least 50 cycles per minute; at least 100 cycles per minute; at least 200 cycles per minute; at least 400 cycles per minute; at least 500 cycles per minute; and/or at least 600 cycles per minute.

In some embodiments, the console is configured to calculate a force applied to the force maintenance assembly based on a shape and size of the ablation element and an angle of attack of the ablation element, wherein the angle of attack is determined from data sensed by an angular displacement sensor of the force maintenance assembly.

In some embodiments, the ablation system further comprises a sheath configured to orient and maintain an orientation of the ablation element relative to the cardiac tissue.

In some embodiments, the sheath is robotically steerable and the system includes a robotic sheath steering apparatus.

In some embodiments, the sheath is configured to maintain the ablation element at a normal apposition to the cardiac tissue.

In some embodiments, the catheter sheath is robotically steerable, advanceable, retractable, and/or otherwise manipulatable to adjust and maintain contact pressure between the ablation element and the cardiac tissue.

In some embodiments, the ablation system comprises robotic catheter actuators used in conjunction with force and contact sensors to maintain constant contact and force between the ablation element and the cardiac tissue.

In some embodiments, the ablation system further comprises a feedback loop configured to generate a feedback signal indicating a change in force and/or a loss of contact used to cause the robotic catheter actuators to compensate.

In some embodiments, the ablation system further comprises one or more wires coupling the robotic catheter actuators to solenoids in a handle positioned on the proximal end of the shaft.

In some embodiments, the ablation system further comprises electro-active polymers configured to change shape and exert a load in response to a current to maintain constant contact and force between the ablation element and the cardiac tissue.

In some embodiments, the ablation system further comprises a feedback loop configured to provide feedback signal indicating a change in force and/or a loss of contact used to cause the electro-active polymer to compensate.

According to another aspect of the inventive concept, provided is an ablation system test fixture, comprising a dynamically movable surface having at least one convex surface configured to receive an ablation element at a distal end of an ablation catheter and a holder configured to hold the ablation catheter to orient and maintain the ablation element in contact with the dynamically movable surface. The dynamically movable surface is deformable to mimic cardiac tissue.

In some embodiments, the dynamically movable surface comprises at least one convex surface.

In some embodiments, the dynamically movable surface comprises at least one dimple or depression configured to receive the ablation element.

According to another aspect of the inventive concept, provided is a method of performing an ablation procedure comprising: selecting an ablation system according to any claim herein; advancing the ablation catheter into the heart of a patient; applying force between the ablation element and cardiac tissue via the force maintenance assembly; and a console delivering ablation energy to tissue with the ablation element.

In some embodiments, the ablation method further comprises a contact sensor of the ablation catheter producing a signal representative of the amount of contact between the ablation element and tissue.

In some embodiments, the ablation method further comprises determining whether the ablation element is in contact with the cardiac tissue, based, at least in part, on the signal from the contact sensor.

In some embodiments, the ablation method further comprises differentiating sufficient contact versus insufficient contact for ablation, based, at least in part, on the signal from the contact sensor, wherein sufficient contact and insufficient contact is determined based on a threshold contact level.

In some embodiments, the ablation method further comprises determining a quantified contact amount from among a range of contact values, based, at least in part, on the signal from the contact sensor.

In some embodiments, the contact sensor is chosen from a group consisting of: a piezoelectric strain sensor, a piezoelectric acoustic sensor, an impedance contact sensor, an electrode contact sensor, a pressure contact sensor, or an optical sensor.

In some embodiments, the contact sensor is or includes at least one piezoelectric strain sensor generating a charge when under a compressive load.

In some embodiments, the at least one piezoelectric strain sensor is a plurality of piezoelectric strain sensors, the system comparing voltages from the plurality of piezoelectric strain sensors to determine an angular orientation of the ablation element with respect to the catheter shaft.

In some embodiments, the contact sensor is or includes at least one impedance contact sensor measuring impedance, wherein a decrease in impedance indicates tissue contact.

In some embodiments, the contact sensor is or includes at least one electrode contact sensor comprising a pair of electrodes, wherein a change in a signal between electrodes in the pair of electrodes indicates tissue contact and/or a mechanical stimulus applied to the force maintenance assembly.

In some embodiments, the ablation method further comprises monitoring the pair of electrodes for signal changes.

In some embodiments, the ablation method further comprises determining a proximity of the ablation element to the cardiac tissue based on the signal changes.

In some embodiments, the ablation method further comprises determining if there is contact of the ablation element with the cardiac tissue based on the signal changes.

In some embodiments, the ablation method further comprises determining an angle of attack of the ablation element with respect to the cardiac tissue based on the signal changes.

In some embodiments, the ablation method further comprises injecting a signal through the catheter to enable contact sensing using the pair of electrodes.

In some embodiments, the contact sensor is or includes at least one pressure contact sensor, the method further comprising measuring irrigation flow to determine tissue contact, wherein blocked irrigation channels within the shaft causes sensed pressure to rise indicating contact.

In some embodiments, the ablation catheter further comprises a handle positioned on the proximal end of the shaft.

In some embodiments, the handle comprises at least one control.

In some embodiments, the ablation method further comprises the handle communicating with the force maintenance assembly.

In some embodiments, the ablation method further comprises the handle mechanically, electro-mechanically, and/or electrically controlling the force maintenance assembly.

In some embodiments, the ablation catheter further comprises at least one mapping electrode and the method includes measuring cardiac activity of the heart.

In some embodiments, the at least one mapping electrode comprises a ring electrode.

In some embodiments, the at least one mapping electrode is positioned on the shaft distal portion.

In some embodiments, the at least one mapping electrode is positioned on the ablation catheter distal portion.

In some embodiments, the at least one mapping electrode comprises a mapping electrode positioned a fixed distance from the ablation element.

In some embodiments, the force maintenance assembly comprises a translatable portion, and wherein the ablation element and the mapping electrode are positioned on the translatable portion.

In some embodiments, the ablation element comprises an electrode, and the method includes gathering bipolar biopotential data between the ablation element and the mapping electrode.

In some embodiments, the ablation catheter further comprises an irrigation lumen and the method includes delivering fluid to tissue proximate the ablation element.

In some embodiments, the irrigation lumen exits at a location proximal to the ablation element.

In some embodiments, the ablation element comprises at least one hole through which the irrigation lumen exits.

In some embodiments, the ablation method further comprises delivering the fluid through the irrigation lumen.

In some embodiments, the ablation method further comprises the fluid lubricating the force maintenance assembly.

In some embodiments, the ablation method further comprises the fluid cooling the ablation element and/or tissue.

In some embodiments, the ablation catheter further comprises an articulating tip assembly.

In some embodiments, the articulating tip assembly comprises a spherical member and a cavity rotatably engaging the spherical member.

In some embodiments, the force maintenance assembly comprises a floating tip portion at the catheter distal end, and wherein the ablation element is positioned on the force maintenance assembly floating tip portion.

In some embodiments, the ablation element is positioned on the distal portion of the shaft.

In some embodiments, the ablation element comprises at least one electrode.

The ablation method according to claim 224, further comprising the ablation element delivering radio frequency (RF) energy to tissue.

The ablation method according to claim 187, or any claim herein, further comprising the ablation element delivering energy to tissue.

The ablation method according to claim 226, further comprising the ablation element delivering energy to tissue in a form selected from the group consisting of: thermal energy; heat energy; cryogenic energy; electromagnetic energy; radio frequency (RF) energy; light energy; light energy provided by a laser; sound energy; subsonic energy; ultrasonic energy; chemical energy; and combinations thereof.

The ablation method according to claim 187, or any claim herein, wherein the ablation catheter further comprises a handle, and wherein the force maintenance assembly is positioned in the handle.

In some embodiments, the force maintenance assembly is positioned in the shaft.

In some embodiments, the force maintenance assembly is positioned on the distal end of the shaft.

In some embodiments, the ablation method further comprises axially aligning the force maintenance assembly with a portion of the shaft.

In some embodiments, the force maintenance assembly is axially aligned with a distal portion of the shaft.

In some embodiments, the ablation method further comprises the force maintenance assembly absorbing mechanical shock.

In some embodiments, the ablation method further comprises the force maintenance assembly dynamically responding to movement of the heart wall.

In some embodiments, the ablation method further comprises the force maintenance assembly compressing up to a max compression distance, and wherein the max compression distance comprises a length between 0.1 mm and 10 mm.

In some embodiments, the ablation method further comprises the force maintenance assembly compressing up to a max compression distance between 0.1 mm and 5 mm.

In some embodiments, the ablation method further comprises the force maintenance assembly compressing over a travel distance, and the force maintenance assembly providing a pre-determined force over the travel distance.

In some embodiments, the ablation method further comprises the force maintenance assembly providing a constant force over the travel distance.

In some embodiments, the ablation method further comprises the force maintenance assembly providing a force that varies over the travel distance.

In some embodiments, the ablation method further comprises the force maintenance assembly providing a force that varies within a pre-determined range over the travel distance.

In some embodiments, the ablation method further comprises the force maintenance assembly providing a force between 5 gmf and 30 gmf over the travel distance.

In some embodiments, the ablation method further comprises the force maintenance assembly providing a force between 10 gmf and 30 gmf over the travel distance.

In some embodiments, the ablation catheter comprises a first ablation catheter as described above, wherein the system comprises a second ablation catheter comprising: a second shaft including a proximal end, a distal portion and a distal end; a second ablation element configured to deliver energy to tissue; and a second force maintenance assembly comprising a second force maintenance element and configured to control and/or assess contact force between the second ablation element and cardiac tissue. The method further comprises: using the first ablation catheter in an atria of the heart and using the second ablation catheter in a ventricle of the heart. The first ablation catheter force maintenance assembly comprises a shorter max compression distance than the max compression distance of the second ablation catheter second force maintenance assembly max compression distance.

In some embodiments, the second catheter second force maintenance assembly max compression distance is at least 1 mm longer than the first catheter force maintenance assembly max compression distance.

In some embodiments, the ablation method further comprises the ablation catheter treating an atria of the heart, and the force maintenance assembly providing a max compression distance selected from the group consisting of: a distance less than 10 mm; a distance less than 5 mm; a distance less than or equal to 3 mm; a distance of between 2 mm and 3 mm; and combinations thereof.

In some embodiments, the ablation catheter is configured to treat a ventricle of the heart, and wherein the force maintenance assembly is configured to provide a max compression distance of between 4 mm and 6 mm.

In some embodiments, the ablation method further comprises a locking element locking the force maintenance assembly to prevent linear and/or angular movement of the ablation element with respect to the shaft.

In some embodiments, the force maintenance assembly further comprises at least one displacement sensor producing a signal correlating to a travel distance of the force maintenance assembly.

In some embodiments, the ablation method further comprises determining when the travel distance is equal to the max compression distance based on the sensor signal.

In some embodiments, the displacement sensor is a capacitive sensor.

In some embodiments, the displacement sensor is an inductive spring sensor, and the method includes using synchronous demodulation to determine displacement.

In some embodiments, the displacement sensor is a linear variable differential transformer (LVDT).

In some embodiments, the ablation method further comprises continuing to provide energy to the ablation element when the travel distance reaches the maximum compression distance.

In some embodiments, the ablation method further comprises limiting the providing of energy to the ablation element, when the travel distance reaches the maximum compression distance.

In some embodiments, the ablation method further comprises stopping the providing of energy to the ablation element, when the travel distance reaches the maximum compression distance.

In some embodiments, the ablation method further comprises at least one displacement sensor configured to determine a linear and/or angular displacement, with respect to the shaft, of a floating tip portion of the ablation catheter comprising the ablation element.

In some embodiments, the at least one displacement sensor is selected from a group consisting of: a capacitive sensor, a tactile sensor, a linear potentiometer, a (linear variable differential transformer) LVDT sensor, a Hall effect sensor, an optical sensor, a load cell, and an indicative sensor.

In some embodiments, the at least one displacement sensor is or includes a capacitive sensor, wherein displacement of the floating tip portion causes changes in capacitance sensed by capacitive elements of the capacitive sensor that are proportional to changes in distance of the floating tip portion.

In some embodiments, the force maintenance assembly includes a bellows surrounding the capacitive sensor and the method includes the bellows serving as a shock absorber.

In some embodiments, the ablation method further comprises calculating a force applied to the force maintenance assembly from a spring force of the bellows and a displacement measured by the capacitive sensor.

In some embodiments, the at least one displacement sensor is or includes a linear displacement sensor, and the method includes using electromagnetic coupling between stationary sensor elements on the shaft and movable sensor elements on the floating tip portion to determine linear displacement.

In some embodiments, the at least one displacement sensor is or includes a LVDT sensor and the method includes measuring linear displacement of the floating tip portion with respect to the catheter shaft using the LVDT sensor.

In some embodiments, the force maintenance assembly includes a bellows surrounding the LVDT sensor and the method includes the bellows serving as a shock absorber.

In some embodiments, the ablation method further comprises calculating a force applied to the force maintenance assembly from a spring force of the bellows and a displacement measured by the LVDT sensor.

In some embodiments, the at least one displacement sensor is or includes a tactile sensor, wherein displacement of the floating tip portion causes contact with a tactile sensor within the catheter shaft.

In some embodiments, the at least one displacement sensor is or includes an optical sensor, wherein the shaft includes a light source and a light sensor and the floating tip portion includes a movable element having a light blocking element, the light blocking element at least partially obstructing light from the light source from passing to the light sensor when the force maintenance assembly is compressed.

In some embodiments, the light blocking element includes a tapered slit opening that increasingly obstructs light from the light source as the force maintenance assembly is increasingly compressed.

In some embodiments, the at least one displacement sensor is or includes a load cell, wherein the load cell is attached to the floating tip portion.

In some embodiments, the at least one displacement sensor is or includes one or more inductive sensor.

In some embodiments, the inductive sensor is configured to determine one or more of linear displacement, angular displacement, overall position, and/or orientation of a movable portion of the force maintenance assembly.

In some embodiments, the inductive sensor comprises one or more coils distributed within the force maintenance assembly.

In some embodiments, the force maintenance assembly includes a plunger movable within the catheter shaft and the inductive sensor includes ferrite tape wrapped around a portion of the plunger and ferrite tape wrapped around a portion of the catheter shaft.

In some embodiments, the movement of the plunger within the shaft changes a self-inductance of the inductive sensors.

In some embodiments, the changes in the self-inductance of the inductive sensors occurs in a stepped manner.

In some embodiments, the inductive sensor includes at least three coils, and the method includes detecting lateral components of a force applied to the force maintenance assembly using the at least three coils.

In some embodiments, the inductive sensor includes at least one coil at the distal end of the catheter shaft, and the method includes measuring axial components of a force applied to the force maintenance assembly using the at least one coil.

In some embodiments, the ablation method further comprises electromagnetically tuning a stiffness and a position of a floating tip portion of the force maintenance assembly in response to a feedback signal induced by compression and expansion of the force maintenance assembly.

In some embodiments, the ablation method further comprises the inductive sensor measuring a resonant frequency change using IQ demodulation to determine contact of the ablation element with the cardiac tissue.

In some embodiments, the at least one displacement sensor includes a displacement sensor in the handle.

In some embodiments, the at least one displacement sensor includes a displacement sensor in the proximal end of the shaft.

In some embodiments, the at least one displacement sensor includes a displacement sensor in the distal end of the shaft.

In some embodiments, the at least one displacement sensor includes one or more displacement sensor in the shaft between the proximal and distal ends of the shaft.

In some embodiments, the ablation system comprises hydraulic fluid, and wherein the force maintenance element comprises a hydraulic piston into which the hydraulic fluid is delivered.

In some embodiments, the ablation method further comprises delivering the hydraulic fluid to the cardiac tissue.

In some embodiments, the hydraulic piston comprises a chamber and an exterior surface, the method further comprising delivering the hydraulic fluid to the chamber of the hydraulic piston and to the exterior surface of the hydraulic piston.

In some embodiments, the ablation method further comprises delivering the hydraulic fluid to the hydraulic piston.

In some embodiments, the console comprises a fluid delivery device, the method including the console controlling delivery of the hydraulic fluid.

In some embodiments, the ablation method further comprises the fluid delivery device delivering the hydraulic fluid to cardiac tissue under control of the console.

In some embodiments, the fluid delivery device comprises a device selected from the group consisting of: peristaltic pump; syringe pump; gravity-feed flow controller; and combinations thereof.

In some embodiments, the fluid delivery device comprises a pump, and the ablation system further comprising an accumulator located downstream of the pump, the method including reducing and/or minimizing a pulsatile nature of the pump using the accumulator.

In some embodiments, the hydraulic fluid comprises saline.

In some embodiments, the force maintenance element comprises a spring or spring material.

In some embodiments, the spring comprises a constant force spring.

In some embodiments, the constant force spring comprises a Nitinol spring material.

In some embodiments, the spring has a shape that minimizes outer diameter growth when compressed.

In some embodiments, the ablation method further comprises the spring providing a force range with a maximum force from a plurality of different angles.

In some embodiments, the spring material comprises a super-elastic polymer.

In some embodiments, the super-elastic polymer comprises polymers of varying durometers arranged in parallel and/or in serial within the catheter shaft.

In some embodiments, the spring material comprises resiliently biased bellows.

In some embodiments, the force maintenance assembly further comprises a piston, and wherein the spring engages the piston.

In some embodiments, the ablation method further comprises the shaft slidingly engaging the piston.

In some embodiments, the piston comprises a flange, the method including the flange engaging the shaft to limit translation of the piston distally.

In some embodiments, the piston comprises a lumen.

In some embodiments, the force maintenance assembly further comprises a deflection sensor.

In some embodiments, the ablation catheter includes a floating tip portion comprising the ablation element, and the method includes the deflection sensor measuring an angle and/or magnitude of deflection of the floating tip portion with respect to a known axis of the shaft.

In some embodiments, the console further comprises a force maintenance module.

In some embodiments, the ablation method further comprises the force maintenance module adjusting the force maintenance assembly.

In some embodiments, the ablation method further comprises the force maintenance module providing a control signal to the force maintenance assembly.

In some embodiments, the force maintenance assembly comprises a hydraulic piston, and the method includes the force maintenance assembly controlling a parameter selected from the group consisting of: fluid flow to the hydraulic piston; fluid pressure within the hydraulic piston; and combinations thereof.

In some embodiments, the console further comprises a processor including at least one algorithm.

In some embodiments, the ablation method further comprises the algorithm adjusting the force maintenance assembly.

In some embodiments, the catheter further comprises a sensor, the method including the sensor providing a signal to the algorithm.

In some embodiments, the ablation method further comprises the sensor signal correlating to the travel distance of the force maintenance assembly.

In some embodiments, the ablation method further comprises the algorithm disabling delivery of energy to the ablation element when the travel distance reaches the max compression distance.

In some embodiments, the console comprises a manual override, and the method includes the manual override allowing delivery of energy to the ablation element when the travel distance reaches the max compression distance.

In some embodiments, the ablation method further comprises the algorithm generating a notification for output to a clinician when the travel distance reaches the maximum compression distance.

In some embodiments, the ablation method further comprises allowing continued energy delivery to the ablation element when the travel distance reaches the maximum compression distance.

In some embodiments, the ablation method further comprises the algorithm generating a notification for output to a clinician when the travel distance is below a minimum distance.

In some embodiments, the ablation method further comprises the sensor signal correlating to the force applied to the cardiac tissue by the ablation element.

In some embodiments, the ablation method further comprises detecting if the force is below a threshold.

In some embodiments, the ablation method further comprises detecting if the force is below a threshold selected from the group consisting of: 1 gmf; 3 gmf; 5 gmf; 7 gmf; 10 gmf and combinations thereof.

In some embodiments, the ablation method further comprises providing an alert if the force falls below the threshold.

In some embodiments, the ablation method further comprises preventing delivery of energy by the ablation element if the force falls below the threshold.

In some embodiments, the ablation method further comprises the algorithm disablesing delivery of energy to the ablation element when contact between the ablation element and tissue is below a threshold.

In some embodiments, the console comprises a manual override, and the method includes allowing delivery of energy to the ablation element when contact between the ablation element and the cardiac tissue is below the threshold using the manual override.

In some embodiments, the console further comprises a user interface.

In some embodiments, the user interface comprises a user input component selected from the group consisting of: joystick; keyboard; mouse; touchscreen; and combinations thereof.

In some embodiments, the user interface comprises a display.

In some embodiments, the ablation method further comprises providing information on the display representing a level of contact between the ablation element and tissue.

In some embodiments, the provided information comprises information selected—from the group consisting of: sufficient contact achieved; insufficient contact achieved; level of force achieved; level of pressure achieved; and combinations thereof.

In some embodiments, the ablation method further comprises providing radio frequency (RF) energy to the ablation element.

In some embodiments, the RF energy is delivered by an energy delivery module comprising a device selected from the group consisting of: RF generator; light energy delivery unit; cryogenic energy delivery unit; ultrasound energy delivery unit; and combinations thereof.

In some embodiments, the ablation system further comprises at least one functional element.

In some embodiments, the at least one functional element comprises one or more transducers selected from the group consisting of: heating element; cooling element; vibrational transducer; ultrasound transducer; electrode; light delivery element; drug or other agent delivery element; and combinations thereof.

In some embodiments, the at least one functional element comprises one or more sensors selected from the group consisting of: a physiologic sensor; a blood pressure sensor; a blood gas sensor; a pressure sensor; a strain gauge; a force sensor; a chemical sensor; an impedance sensor; a magnetic sensor; an electrode; a displacement sensor; and combinations thereof.

In some embodiments, the ablation method further comprises a mapping catheter.

In some embodiments, the mapping catheter comprises an expandable assembly comprising multiple electrodes.

In some embodiments, the expandable assembly further comprises multiple ultrasound transducers.

In some embodiments, the mapping catheter further comprises at least one functional element.

In some embodiments, the console further comprises a mapping module operably interfacing with the mapping catheter.

In some embodiments, the mapping module comprises an ultrasound module, and the method includes recording and/or processing ultrasound information.

In some embodiments, the mapping module comprises a biopotential module, and the method includes recording and/or processing biopotential information.

In some embodiments, the ablation method further comprises at least one patient patch.

In some embodiments, the ablation further comprises the at least one patient patch transmitting and/or receiving electrical signals through and/or from the patient.

In some embodiments, the force maintenance assembly comprises a plurality of compression areas from the handle to the ablation element.

In some embodiments, the plurality of compression areas includes one or more hydraulic, spring, and/or magnetic force maintenance elements.

In some embodiments, the force maintenance element comprises a hook or a barb configured to selectively pierce the cardiac tissue.

In some embodiments, the force maintenance element comprises a vacuum, and the method includes the vacuum selectively applying suction to the cardiac tissue to control or maintain contact with the ablation element.

In some embodiments, the force maintenance element comprises a cryogenic element, and the method includes the cryogenic element cryogenically sticking to the cardiac tissue.

In some embodiments, the ablation element is a cryogenic ablation element, and the method includes the cryogenic ablation element cryogenically sticking to the cardiac tissue.

In some embodiments, the force maintenance assembly comprises at least one pair of magnets positioned with opposing polarities directed toward each other so that the magnets repel each other to generate a spring force.

In some embodiments, the ablation further comprises generating a constant spring force the at least one pair of magnets.

In some embodiments, a floating tip portion of the ablation catheter comprises the ablation element and is coupled to the shaft by the force maintenance assembly, and the at least one pair of magnets is oriented to bias the floating tip portion in a straight orientation relative to the shaft.

In some embodiments, the ablation method further comprises a bellows surrounding at least a portion of the force maintenance element.

In some embodiments, the bellows forms a part of the force maintenance assembly and provides a spring force.

In some embodiments, the ablation further comprises the bellows shielding the force maintenance element from in-flow of biological material.

In some embodiments, the bellows is formed of a thin-walled elastomer, TPU, or TPV to avoid adding stiffness to the force maintenance assembly.

In some embodiments, the bellows is fainted of a pre-stretched silicon extrusion, which is configured not to bunch when compressed.

In some embodiments, the catheter includes one or more wires running between the force maintenance assembly and the handle through the shaft and the one or more wires are coiled to minimize resistance when the force maintenance assembly is compressed.

In some embodiments, the ablation method further comprises calculating a force applied to the force maintenance assembly based on a shape and size of the ablation element and an angle of attack of the ablation element, wherein the angle of attack is determined from data sensed by an angular displacement sensor of the force maintenance assembly.

In some embodiments, the ablation method further comprises a sheath, and the method includes orienting and maintaining an orientation of the ablation element relative to the cardiac tissue.

In some embodiments, the system includes a robotic sheath steering apparatus, and the method includes robotically steering the sheath.

In some embodiments, the ablation method further comprises maintaining the ablation element at a normal apposition to the cardiac tissue using the sheath.

In some embodiments, the ablation method further comprises robotically steering the catheter sheath to adjust and maintain contact pressure between the ablation element and the cardiac tissue.

In some embodiments, the ablation further comprises maintaining constant contact and force between the ablation element and the cardiac tissue using robotic catheter actuators in conjunction with force and contact sensors.

In some embodiments, the ablation method further comprises generating a feedback signal indicating a change in force and/or a loss of contact used to cause the robotic catheter actuators to compensate.

In some embodiments, the ablation method further comprises one or more wires coupling the robotic catheter actuators to solenoids in a handle positioned on the proximal end of the shaft.

In some embodiments, the ablation system comprises electro-active polymers configured to change shape and exert a load in response to a current, and the method includes using the electro-active polymers to maintain constant contact and force between the ablation element and the cardiac tissue.

In some embodiments, the ablation method further comprises providing a feedback signal indicating a change in force and/or a loss of contact used to cause the electro-active polymer to compensate.

According to aspects of the inventive concept, provided is an ablation system test method, comprising: providing an ablation system test fixture according to any claim herein; holding an ablation catheter in a holder to orient and maintain the ablation element in contact with a dynamically movable surface of the ablation system test fixture; wherein the dynamically movable surface is deformable to mimic cardiac tissue; applying energy to an ablation element of the ablation system; and analyzing performance of the ablation system.

In some embodiments, the dynamically movable surface comprises at least one convex surface.

In some embodiments, the dynamically movable surface comprises at least one dimple or depression configured to receive the ablation element.

According to aspects of the inventive concept, provided is an ablation system having a force maintenance assembly as shown and described.

According to aspects of the inventive concept, provided is an ablation method of an ablation system having a force maintenance assembly as shown and described.

According to aspects of the inventive concept, provided is an ablation system test fixture as shown and described.

According to aspects of the inventive concept, provided is an ablation system test method as shown and described.

BRIEF DESCRIPTION OF THE DRAWINGS

FIG. 8 illustrates a perspective view of the distal portion of an ablation catheter comprising a force maintenance assembly that includes a hydraulic piston, consistent with the present inventive concepts.

FIGS. 8A and 8B illustrate side sectional views of the distal portion of the ablation catheter of FIG. 8, consistent with the present inventive concepts.

DETAILED DESCRIPTION OF THE DRAWINGS

Figure 1:
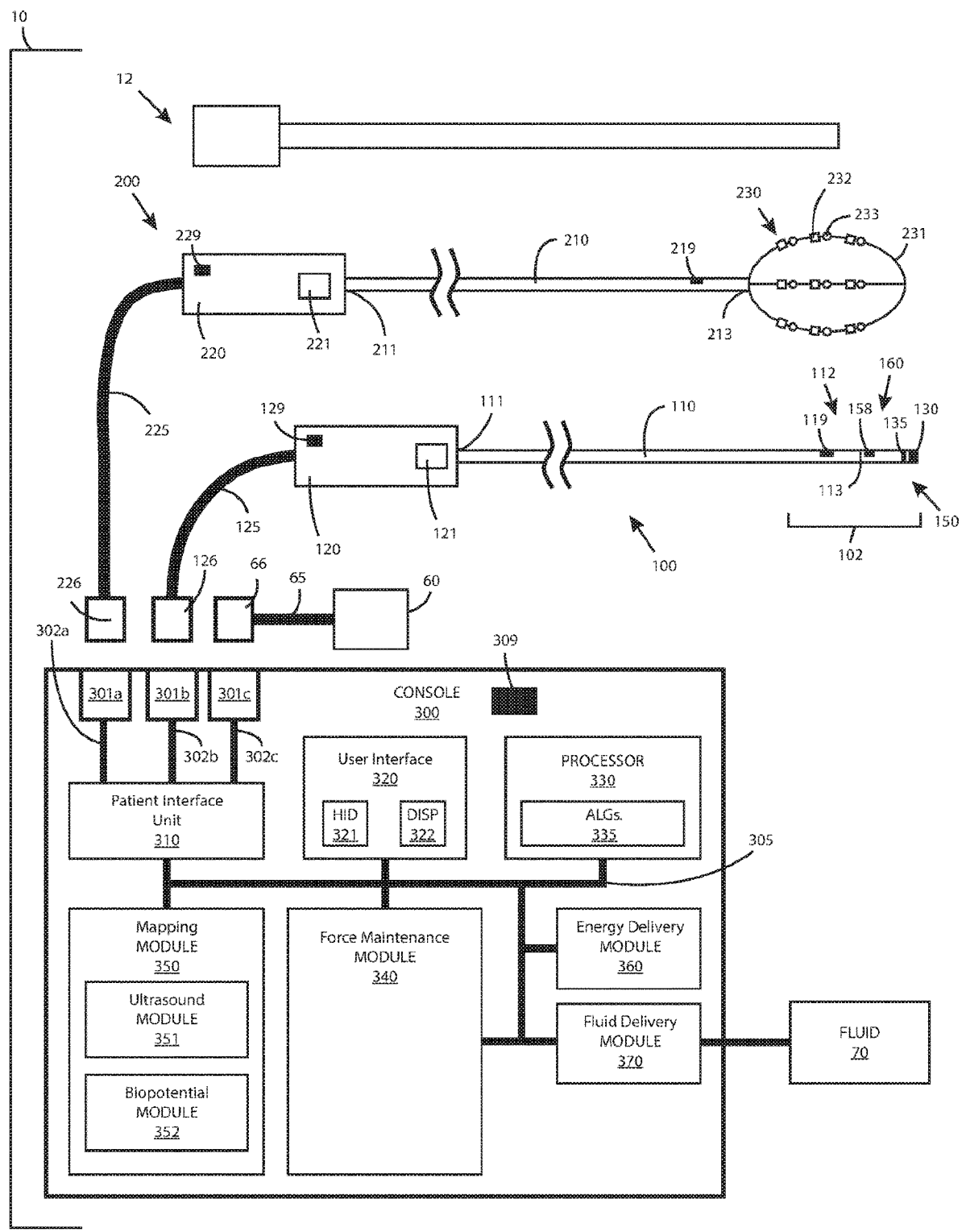
FIG. 1 illustrates a schematic view of a system for performing a medical procedure on a patient, consistent with the present inventive concepts.

Reference will now be made in detail to the present embodiments of the technology, examples of which are illustrated in the accompanying drawings. The same reference numbers are used throughout the drawings to refer to the same or like parts.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers, and/or sections, these limitations, elements, components, regions, layers, and/or sections should not be limited by these terms. These terms are only used to distinguish one limitation, element, component, region, layer or section from another limitation, element, component, region, layer or section.

Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on", and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate" shall include locations relatively close to, on, in, and/or within a referenced component or other location.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence.

The term "and/or" where used herein is to be taken as specific disclosure of each of the two specified features or components with or without the other. For example "A and/or B" is to be taken as specific disclosure of each of (i) A, (ii) B, and (iii) A and B, just as if each is set out individually herein.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

Provided herein are systems, methods and devices for performing a medical procedure on a patient. An ablation catheter comprises a shaft and one or more ablation elements, such as an electrode or other ablation element positioned at the distal end of the catheter. The one or more ablation elements can be configured to deliver energy to tissue, such as to ablate the tissue. The ablation catheter further comprises a force maintenance assembly configured to limit, maintain, control, and/or assess the contact force between the ablation element and tissue. In some embodiments, the ablation catheter is configured to ablate cardiac tissue, such as in a cardiac ablation procedure used to treat an arrhythmia of the patient. The system can include a console configured to operably attach to the ablation catheter. The console can include an energy delivery assembly configured to provide energy to the one or more ablation elements.

Referring now to FIG. 1, a schematic view of a system for performing a medical procedure on a patient is illustrated, consistent with the present inventive concepts. The medical procedure can comprise a diagnostic procedure, a therapeutic procedure, or a combined diagnostic and therapeutic procedure. System 10 can comprise one or more ablation catheters 100, one or more mapping catheters 200, one or more sheaths 12, one or more patient patches 60, and a console 300 which operably attaches (e.g. electrically, mechanically, fluidly, sonically, and/or optically attaches) to the one or more catheters 100, 200 (e.g., two, three or more catheters 100, 200), and the one or more patient patches 60.

Ablation catheter 100 includes shaft 110, typically a flexible shaft, including proximal end 111, distal portion 112, and distal end 113. An operator graspable portion, handle 120, is positioned on proximal end 111 of shaft 110. Handle 120 can comprise one or more controls (e.g. one or more buttons, switches, levers, and the like), such as control 121 shown in FIG. 2. Ablation catheter 100 can comprise an assembly configured to measure, monitor, react to, and/or maintain a force (e.g. a force between tissue and one or more portions of catheter 100), such as force maintenance assembly 150. Force maintenance assembly 150 can be positioned within handle 120, within a portion of shaft 110 (e.g. the distal portion 112 of shaft 110), and/or on the distal end 113 of shaft 110 (as shown). Force maintenance assembly 150 can comprise one or more force maintenance elements 160, as described herebelow. Force maintenance assembly 150 can also comprise one or more sensing elements 158, which can take the form of or include one or more sensors. As examples, such force maintenance elements 160 can be or include one or more of: a hydraulic element, a spring, a magnet, a compressible fluid, a memory material, and the like. The force maintenance elements 160 can be located at a distal end, proximal end, or intermediate portion of the ablation catheter 100, or a combination of two or more thereof.

Force maintenance assembly 150 can be axially aligned with shaft 110 (e.g. a major axis of force maintenance assembly 150 is aligned with a central axis of distal portion 112), such as when aligned with distal portion 112. Force maintenance assembly 150 can be configured to absorb mechanical shocks, and/or can be configured to dynamically (e.g. dynamically and automatically) respond to movement of the heart wall or other cardiac tissue (e.g. avoiding reliance on the clinician to manually react to the movement of the endocardial surface in a cardiac ablation procedure). The force maintenance assembly 150 can allow for high and/or low frequency responses, various response ranges, etc. Force maintenance assembly 150 can be configured to compress over a "travel distance" (also referred to as the "compression distance" and equal to the distance force maintenance assembly 150 compresses when a force is applied) up to a pre-determined maximum distance (the "max compression distance" or "max travel distance"), such as a maximum distance between 0.1 mm to 10 mm, a maximum distance between 0.1 mm and 5 mm, or some other predetermined distance range and/or limit.

Force maintenance assembly 150 can be configured to provide a pre-determined force range over all or a portion of the travel distance, for example a pre-determined constant and/or variable force between 0.1 gmf and 100 gmf, between 5 gmf and 30 gmf, or between 10 gmf and 30 gmf. In some embodiments, force maintenance assembly 150 is configured to provide a relatively constant force over all or a portion of the travel distance, for example a pre-determined constant force between 0.1 gmf and 100 gmf, such as between 5 gmf and 30 gmf, or between 10 gmf and 30 gmf. Additionally or alternatively, in some embodiments force maintenance assembly 150 is configured to provide a variable force over all or a portion of the travel distance, such as a variable force that varies within a pre-determined range of forces (e.g. a range of forces proportional to the amount compressed). For example, force maintenance assembly 150 can be configured to apply a force that varies between 5 gmf and 30 gmf, such as a force that varies between 10 gmf and 30 gmf.

Force maintenance assembly 150 can include one or more sensing elements or sensors, such as sensing element 158 shown, configured to produce a signal correlating to the amount of compression of the force maintenance assembly. Additionally or alternatively, sensing element 158 can be configured to produce a signal correlating to maximum compression of force maintenance assembly 150. Ablation catheter 100 comprises one or more elements configured to deliver ablation energy to tissue, ablation element 130, such as an electrode configured to deliver RF energy to tissue. Ablation element 130 can be configured to deliver a form of energy selected from the group consisting of: electromagnetic energy, such as RF energy or microwave energy; light energy, such as laser light energy; cryogenic energy; ultrasound energy; and combinations thereof. In some embodiments, ablation element 130 delivers at least two forms of energy selected from the group consisting of: electromagnetic energy; RF energy; microwave energy; light energy; laser light energy; cryogenic energy; ultrasound energy; and combinations thereof. Ablation element 130 can be positioned on the distal portion of ablation catheter 100, such as catheter distal portion 102. Ablation element 130 can include at least one ablation element (e.g. at least one electrode, at least one optical element configured to deliver light energy, and/or at least one cryogenic fluid delivery element) positioned on the distal end of ablation catheter 100, in a "tip electrode" configuration. For example, ablation element 130 can be positioned on distal end 113 of shaft 110, such as when force maintenance assembly 150 is positioned within shaft 110. Alternatively, ablation element 130 can be positioned on the distal end of the force maintenance assembly 150. In some embodiments, ablation catheter 100 can comprise two, three, or more ablation elements 130, such as multiple electrodes configured to deliver monopolar and/or bipolar electromagnetic (e.g. RF) ablation energy to ablate tissue.

Ablation catheter 100 can be configured for ablation of the atria (e.g. to treat atrial fibrillation or right atrial flutter) and/or the ventricles of the heart (e.g. to treat ventricular tachycardia). For ablation of the atria, force maintenance assembly 150 can be configured with a first max compression distance, such as a distance less than or equal to 10 mm, less than or equal to 5 mm, or less than or equal to 3 mm. Alternatively, for ablation of the ventricles, force maintenance assembly 150 can be configured with a second max compression distance, such as a distance greater than the first max compression distance, such as a distance at least 1 mm greater than the first max compression distance, such as a second (ventricular) max compression distance of at least 3 mm or at least 6 mm. In some embodiments, the first (atrial) max compression distance comprises a distance of approximately 2-3 mm. In some embodiments, the second (ventricular) max compression distance comprises a distance of approximately 4-6 mm.

System 10 can include at least a second ablation catheter 100', such as a second ablation catheter 100' configured for use in the atria or ventricles of the heart. In some embodiments, first ablation catheter 100 is configured for use in an atria and second ablation catheter 100' is configured for use in a ventricle. In these embodiments, first ablation catheter 100 can include a force maintenance assembly 150 comprising a shorter max compression distance as compared to the max compression distance of the force maintenance assembly 150 positioned within second ablation catheter 100'.

Ablation catheter 100 can comprise one or more electrodes configured to record biopotential and/or position information, such as mapping electrode 135 shown. Mapping electrode 135 can comprise one or more electrodes positioned on distal portion 102 of ablation catheter 100, as shown. Mapping electrode 135 can comprise a ring electrode. In some embodiments, mapping electrode 135 comprise at least one sensor or sensing element, such as an electrode-based sensor and/or a non-electrode based sensor (e.g. a light sensor, a temperature sensor, a pH sensor, a physiologic sensor such as a blood sensor, a blood gas sensor, and the like).

System 10 can comprise one or more functional elements, such as functional elements 119, 129, 219, 229, and/or 309 shown in FIG. 1 and described in detail herebelow. Functional elements 119, 129, 219, 229, and/or 309 can each comprise one or more sensors and/or one or more transducers, as described herein. In some embodiments, functional elements 119, 129, 219, 229, and/or 309 comprise a transducer selected from the group consisting of: heating element; cooling element; vibrational transducer; ultrasound transducer; electrode; light delivery element; drug or other agent delivery element; and combinations of one or more of these. In some embodiments, functional elements 119, 129, 219, 229, and/or 309 comprise a sensor selected from the group consisting of: a physiologic sensor; a blood pressure sensor; a blood gas sensor; a pressure sensor; a strain gauge; a force sensor; a chemical sensor; an impedance sensor; a magnetic sensor; an electrode; a displacement sensor (e.g. a sensor configured to determine the distance force maintenance assembly 150 is compressed); a flow sensor; and combinations of one or more of these. In some embodiments, functional elements 129 and/or 229 comprise functional elements configured to provide feedback, and/or otherwise alert the user to the status of one or more components of system 10 (e.g. when an undesired condition is present). Functional elements 129 and/or 229 can comprise an element selected from the group consisting of: a haptic transducer; a light source, such as an LED light source; an audio transducer, such as a speaker; and combinations of one or more of these.

Ablation catheter 100 is configured to operably attach to console 300. Ablation catheter 100 comprises conduit 125 and attached connector 126. Connector 126 operably attaches to a mating connector, connector 301b of console 300. Conduit 125 can comprise one or more wires or conductive traces ("wires" herein), optical fibers, tubes (e.g. hydraulic, pneumatic, irrigation or other fluid delivery tubes), wave guides, and/or mechanical linkages (e.g. translating filament), each of which can be used to operably attach one or more components of console 300 to one or more components of ablation catheter 100.

Mapping catheter 200 of system 10 includes shaft 210, typically a flexible shaft comprising one or more lumens. Positioned on distal end 213 as shown, or positioned at least on a distal portion of shaft 210, is basket assembly 230. An operator graspable portion, handle 220, is positioned on proximal end 211 of shaft 210. Handle 220 can comprise one or more controls, such as control 221 shown.

Basket assembly 230 can comprise an expandable assembly, such as an assembly resiliently biased in a radially expanded or compacted state and configured to correspondingly be compacted or expanded, respectively, such as via control 221, by advancing out of the distal end of a sheath (to radially expand), and/or by being retracted within a sheath (to radially compact), such as sheath 12 or the like. Basket assembly 230 comprises an array of filaments, splines 231, which can comprise metal (e.g. stainless steel and/or nickel titanium alloy) and/or plastic filaments that are resiliently biased (e.g. in an expanded and/or compacted state). Basket assembly 230 can include a plurality of electrodes 232 coupled to splines 231. Additionally or alternatively, basket assembly 230 can include a plurality of ultrasound transducers 233 coupled to splines 231. In some embodiments, basket assembly 230 and/or mapping catheter 200 are of similar construction and arrangement to the similar components described in applicant's co-pending U.S. patent application Ser. No. 14/003,671, titled "Device and Method For the Geometric Determination of Electrical Dipole Densities on the Cardiac Wall", filed Sep. 6, 2013 and/or applicant's co-pending U.S. patent application Ser. No. 14/762,944, titled "Expandable Catheter Assembly with Flexible Printed Circuit Board (PCB) Electrical Pathways", filed Jul. 23, 2015, the content of each of which is included in its entirety for all purposes. In some embodiments, one or more electrodes 232 and/or ultrasound transducers 233 additionally or alternatively include a sensor or sensing element, such as a physiologic sensor and/or other sensor as described herein.

As described above, mapping catheter 200 of system 10 can comprise one or more functional elements, such as functional elements 219, 229 shown, and described hereabove. In some embodiments, one or more functional elements 219 and/or 229 are positioned on basket assembly 230 (e.g. on one or more splines 231).

Mapping catheter 200 is configured to operably attach to console 300. Mapping catheter 200 comprises conduit 225 and attached connector 226. Connector 226 operably attaches to a mating connector, connector 301a of console 300. Conduit 225 can comprise one or more wires, optical fibers, tubes (e.g. hydraulic, pneumatic, irrigation or other fluid delivery tubes), wave guides, and/or mechanical linkages (e.g. translating filament), each of which can be used to operably attach one or more components of console 300 to one or more components of mapping catheter 200.

System 10 can include one or more patch electrodes 60, which can comprise standard skin electrodes and/or other electrodes configured to attach to the skin of the patient and transmit electrical signals through the patient and/or receive electrical signals from the patient. In some embodiments, patch electrodes 60 are configured to record the patient's electrocardiogram (ECG) and/or to transmit and/or receive localization signals of system 10. Patch electrodes 60 operably attach (e.g. electrically attach) to console 300. Patch electrodes 60 comprise conduit 65 (e.g. one or more electrical wires) and attached connector 66. Connector 66 operably attaches to a mating connector, connector 301c of console 300.

Console 300 includes one or more internal components configured to control and/or otherwise interface with the one or more ablation catheters 100, one or more mapping catheters 200, and/or one or more patient patches 60. Console 300 comprises one or more conduits 302, such as conduits 302a, 302b, and/or 302c, which via connectors 301a, 301b, and/or 301c operably connect to the one or more ablation catheters 100, one or more mapping catheters 200, and/or one or more patient patches 60, respectively. Conduits 302 can comprise one or more wires, optical fibers, tubes (e.g. hydraulic, pneumatic, irrigation or other fluid delivery tubes), wave guides, and/or mechanical linkages (e.g. translating filament).

Console 300 can comprise patient interface unit 310. Patent interface unit (PIU) 310 is connected (e.g. electrically connected) to one or more of units 320, 330, 340, 350, and/or 360, each described in detail herebelow, via bus 305. Bus 305 can comprise one or more wires, optical fibers, and/or other conduits configured to provide power, transmit data, and/or receive data. In some embodiments, bus 305 comprises one or more fluid delivery tubes configured to provide hydraulic fluid, irrigation fluid, and/or other fluid as described herein. PIU 310 can be operably attached to 340, 350, 360, 330 and 320, such as to allow power, data, fluids, and/or mechanical linkages to pass between PIU 310 and one or more of: ablation catheter 100, mapping catheter 200, and/or patches 60. In some embodiments, PIU 310 can reduce undesired electrical interaction between two or more modules of console 300. For example, PIU 310 can include one or more filters (e.g. one, two or more parallel LC notch filters and/or low-pass filters) configured to reduce electrical interference between a mapping module and an RF generator, such as interference from signals transmitted into and received from the patient. PIU 310 can include one or more components selected from the group consisting of: a filter; a transformer; a buffer; an amplifier; a pass thru (e.g. a conduit that is unfiltered or otherwise unaltered by PIU 310, such as a fluid conduit); and combinations of one or more of these. In some embodiments, PIU 310 comprises an electrical protection circuit configured to protect console 300 from damage caused by high-energy signals such as defibrillation pulses and/or RF ablation energy delivered to the patient.

Console 300 can comprise user interface unit 320 which includes one or more user input and/or user output components. In some embodiments, user interface unit 320 comprises a joystick, keyboard, mouse, touchscreen, and/or other human interface device, such as human interface device 321. In some embodiments, user interface unit 320 comprises a display, such as display 322.

Console 300 can comprise a signal processing assembly, processor 330. In some embodiments, processor 330 comprises one or more algorithms, such as algorithm 335. Processor 330 can receive a signal, such as a signal from one or more sensors (as described herein) of ablation catheter 100 and/or mapping catheter 200. Processor 330 can be configured to perform one or more mathematical operations on the received signal, and produce a result correlating to a quantitative or qualitative measure of the force applied by ablation catheter 100 to tissue, the amount of compression of force maintenance assembly 150, the orientation of ablation catheter 100, the proximity of a portion of ablation catheter 100 to cardiac tissue, and/or the level or quality of contact between a portion of ablation catheter 100 and cardiac tissue. The one or more mathematical operations can comprise an operation of function selected from the group consisting of: arithmetic operations; statistical operations; linear and/or non-linear functions; operations as a function of time; operations as a function of space or distance; comparison to a threshold; comparison to a range; and combinations of one or more of these. In some embodiments, algorithm 335 is configured to monitor, assess and/or control ("control" herein) force maintenance assembly 150 (e.g. adjust one or more parameters of force maintenance assembly in a closed loop or semi-closed loop fashion), such as control based on the sensor signal. In some embodiments, algorithm 335 is configured to determine and/or assess at least one of contact, force, or pressure applied by ablation catheter 100 to tissue. In some embodiments, algorithm 335 processes one or more signals received from one or more sensors of system 10, such as a signal correlating to: the temperature of the ablation element; the temperature of the tissue surrounding the ablation element; the duration of energy delivery to tissue; the level of energy being delivered to tissue; the force and/or pressure being applied to tissue; and combinations of one or more of these. Algorithm 335 can be configured to modify the energy delivery based on these signals, for example to stop the energy delivery when a combination of sufficient parameter levels has been reached, for example when a sufficient energy delivery at a sufficient pressure for a sufficient period of time has been reached. In some embodiments, system 10 is configured to deliver increased energy levels to decrease duration of energy delivery to tissue. Alternatively or additionally, system 10 can be configured to increase duration of energy delivery to tissue, in order to decrease an energy level. In some embodiments, system 10 controls force between ablation element 130 and tissue to adjust one or more of duration of energy delivery and/or level of energy delivery (e.g. voltage level, current level and/or power level). In some embodiments, system 10 adjusts duration of energy delivery and/or level of energy delivery based on a measured and/or controlled level of force between ablation element 130 and tissue.

Console 300 can comprise fluid delivery module 370 configured to deliver a fluid (e.g. a hydraulic fluid and/or an irrigation fluid as described herein), to ablation catheter 100 and/or mapping catheter 200, such as via PIU 310 as shown. In an alternative embodiment, fluid delivery module 370 is connected to ablation catheter 100 and/or mapping catheter 200 without passing through PIU 310. Fluid delivery module 370 can comprise one or more fluid delivery devices (e.g. peristaltic pump, syringe pump, gravity-feed flow controller and/or other fluid delivery device) which can be attached to one or more sources of saline and/or other fluid, fluid 70.

Console 300 can comprise force maintenance module 340. Force maintenance module 340 can be configured to provide a signal that allows system 10 to adjust force applied by ablation catheter 100 to tissue, such as to provide a control signal to force maintenance assembly 150. In some embodiments, force maintenance module 340 is configured to deliver and/or at least control (e.g. control the pressure of) a supply of hydraulic fluid to ablation catheter 100 (e.g. via fluid delivery module 370).

Console 300 can comprise mapping module 350. In some embodiments, mapping module 350 comprises a module configured to record and/or process ultrasound information, such as ultrasound module 351. In some embodiments, mapping module 350 comprises a module configured to record and process biopotential information, such as biopotential module 352. Mapping module 350 can transmit energy and/or signals to ablation catheter 100, mapping catheter 200, and/or patches 60 via PIU 310 (as shown), or otherwise. Mapping module 350 can be configured to transmit one or more signals into the patient (e.g. via one or more patches 60), such as to create a localization field within the patient. Furthermore, mapping module 350 can receive signals from one or more electrodes (or other sensors) of ablation catheter 100 and/or mapping catheter 200, such as signals correlating to the localization signals, such as to determine the localization of the one or more electrodes within the localization field (e.g. to determine the location and/or orientation of the associated catheter(s) within the patient). In some embodiments, two or more localization fields can be used simultaneously. The components used to generate and/or sense the localization fields (e.g. patches 60 and/or the one or more electrodes of ablation catheter 100 or mapping catheter 200), can be configured to transmit localization signals (herein "source"), receive localization signals (herein "sink"), and/or transmit and receive localization signals interchangeably. For example, the components can be multiplexed to source and sink localization signals between each other in a pattern configured to enhance the localization information received by mapping module 350, such as information regarding the relative position between a component of system 10 and the cardiac tissue or other structures within the cardiac chamber and/or another component of system 10.

For example, the direction of current flow between two or more components used to perform a localization measurement can be reversed. For example, in an impedance-based system, multiple (e.g. 3 or 4) localization fields can be generated simultaneously using multiple frequency ranges. All electrodes and/or sensors within the field can be used to sense the localization field. The components used to source (e.g. transmit the localization signals) and sink (e.g. sense the localization signals) the localization fields can be fixed and static, such as patches 60 positioned on the body surface that are used to source the localization fields, and electrodes located on one or more components of system 10 and positioned within the patient that are used to sink the localization signals. Alternatively, the components can be time-multiplexed and/or frequency-multiplexed, such as by sourcing and sinking current from different sets of components at various frequencies and/or at various times. As an example of a time-multiplexed localization method, the system can include three source/sink components, A-C. In a first configuration, component A is used to source, and component B is used to sink. In a second configuration, B can be used to source and A to sink. In a third configuration, C is used to source, and B is used to sink. These three configurations can be multiplexed to provide an enhanced localization method. Using all possible permutations would provide the full complement of information available via the source-sink configurations. Subsets of these configurations can be selected to reduce electronic and algorithmic complexity, while providing sufficient information to resolve the number of conditions and/or states required. In some embodiments, the electronics are configured to minimize current leakage (e.g. paths to a ground) within a range of frequencies (such as 10-100 kHz) via sensors and/or electrodes present within the field and/or used to measure the field. For example, current leakage can be minimized with the design of a sufficiently high input impedance in the localization frequency range of interest.

In some embodiments, ultrasound module 351 of mapping module 350 is configured to transmit and receive ultrasound signals via one or more ultrasound transducers 233 of mapping catheter 200 to determine the distance between ultrasound transducers 233 and the cardiac tissue, such as to, in coordination with the localization data, generate an anatomical model of the cardiac tissue. Biopotential module 352 of mapping module 350 can be configured to record one or more biopotential signals, such as via electrodes 232 of mapping catheter 200, to create an electrical activity map of the cardiac chamber. In some embodiments, mapping module 350, including ultrasound module 351 and biopotential module 352, are of similar construction and arrangement to the similar components described in applicants co-pending International PCT Patent Application Serial Number PCT/US2016/032017, titled "Ultrasound Sequencing System and Method", filed May 12, 2016, and/or applicant's co-pending International PCT Patent Application Serial Number PCT/US2016/032420, titled "Localization System and Method Useful in the Acquisition and Analysis of Cardiac Information", filed May 13, 2016, the content of each of which is included in its entirety for all purposes.

Console 300 can comprise energy delivery module 360, such as an energy delivery module configured to provide ablation energy to ablation catheter 100 (e.g. provide energy to ablation element 130 comprising one or more electrodes or other ablation elements). Energy delivery module 360 can provide energy to ablation catheter 100 via PIU 310 (as shown), or otherwise. Ablation energy can comprise an energy form selected from the group consisting of: thermal energy, such as heat energy or cryogenic energy; electromagnetic energy, such as radiofrequency (RF) energy and/or microwave energy; light energy, such as light energy provided by a laser; sound energy, such as subsonic energy or ultrasonic energy; chemical energy; and combinations of one or more of these. Energy delivery module 360 can comprise an energy delivery module selected from the group consisting of: RF generator; light energy delivery unit; cryogenic energy delivery unit; ultrasound energy delivery unit; microwave energy delivery unit; electroporation energy delivery unit; and combinations of these. In some embodiments energy delivery module 360 comprises an RF generator configured to provide RF ablation energy to ablation element 130 (i.e. when ablation element 130 comprises an electrode).

In some embodiments, console 300 comprises one or more functional elements, such as functional element 309 shown and described hereabove.

One or more sensors of ablation catheter 100 (e.g. one or more of functional elements 119 or 129 configured as one or more sensors) can be configured to produce a signal correlating to a level of contact between ablation element 130 and tissue (e.g. cardiac tissue). The signal provided can simply differentiate a minimum (sufficient) level of contact versus an insufficient level of contact (e.g. a lack of contact), and/or it can provide data that differentiates various levels of contact (e.g. a quantitative assessment of force between ablation element 130 and tissue). Console 300 can provide qualitative and/or quantitative contact information to a user (e.g. a clinician), such as via display 322, the information indicative of the level of contact between ablation element 130 and tissue (e.g. chamber wall and/or other cardiac tissue). In some embodiments, system 10 is configured to provide (via display 322) information comprising: sufficient contact achieved (e.g. sufficient contact to perform a efficacious delivery of energy to tissue); insufficient contact achieved; level of force achieved; level of pressure achieved; distance or proximity to a boundary; orientation or angle-of-attack to a boundary; topology of a proximate boundary; contact efficiency (as described herebelow); and combinations of one or more of these.

Figure 2:
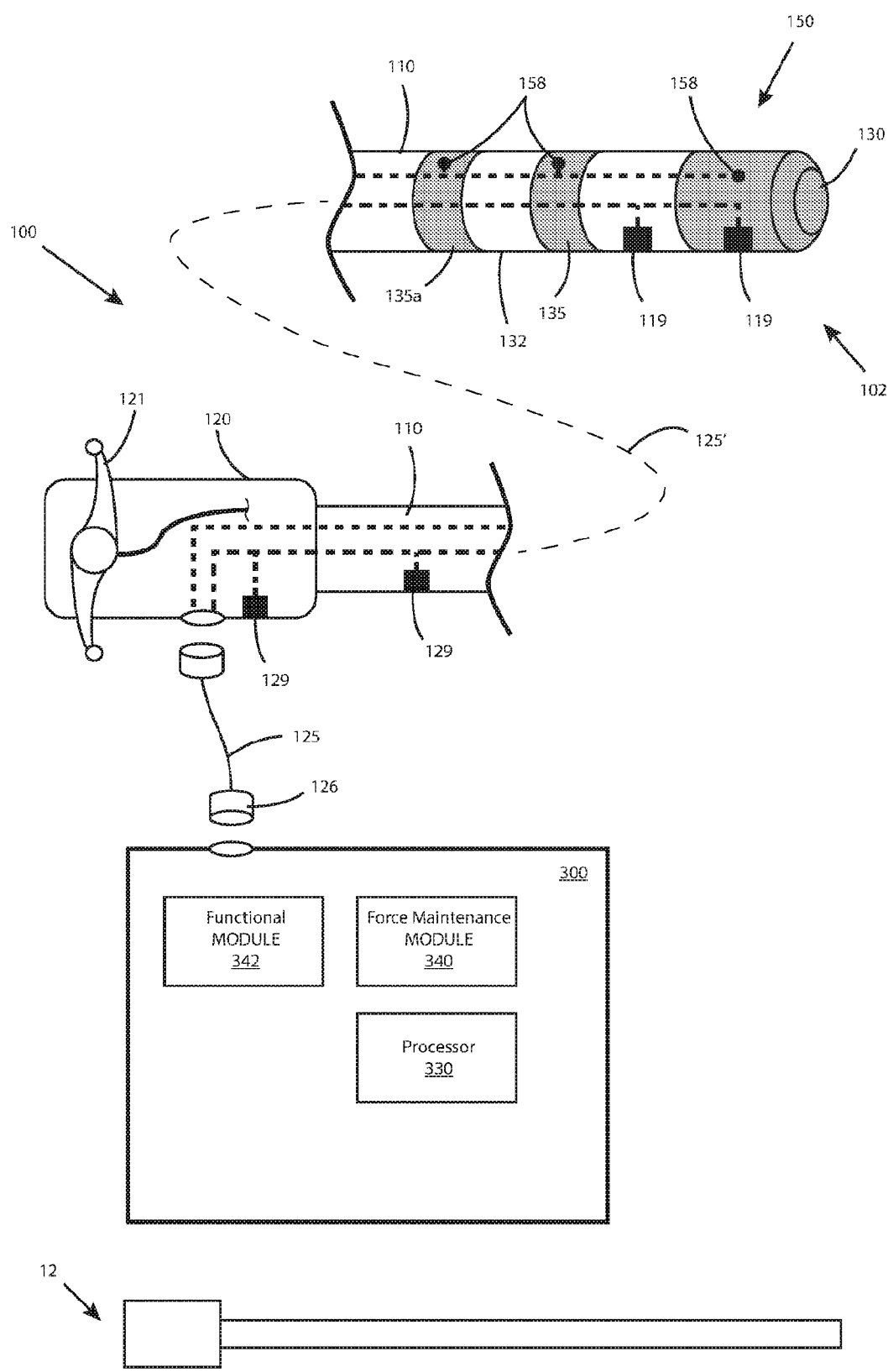
FIG. 2 illustrates a schematic view of a system for performing contact maintenance and sensing, consistent with the present inventive concepts.

Referring now to FIG. 2, a schematic view of a system for performing contact maintenance and sensing is illustrated, consistent with the present inventive concept. In FIG. 2, a distal portion 102 of an ablation catheter 100 is shown, including an ablation element 130 and a force maintenance assembly 150. One or more mapping electrodes 135, 135a separated by an electrical isolator 132 can also be included at the distal portion of the shaft 110, as shown.

The force maintenance assembly 150 can be implemented with contact maintenance and/or sensing functionality. A handle 120 located at the proximal end of shaft 110 of the ablation catheter 100 is also shown. The handle 120 includes a control 121 that enables control, e.g., steering, of the distal portion 102 of the ablation catheter 100, such as for desired placement of the ablation element 130 against tissue that is targeted for treatment. The control 121 in catheter handle 120 can also be used to adjust a force applied by, and/or an effective range of displacement of a "floating tip portion" (as described herebelow) of ablation catheter 100.

A sheath 12 can be used as an introducer catheter to aid in delivering the ablation catheter 100, and optionally a mapping catheter 200, to a cardiac chamber, for example. The sheath 12 can be a conventional sheath (e.g. a conventional transseptal sheath) used in a conventional manner. In some embodiments, sheath 12 comprises a robotically advanced, retracted, steered, and/or otherwise manipulated sheath. The sheath 12 could be used to help orient and/or maintain orientation of the catheter tip relative to the heart wall (e.g. via an included distal portion steering mechanism).

The ablation catheter 100 can be coupled to console 300, which can include a plurality of functional modules, processors, and/or electronic storage devices necessary and/or useful for performing ablation, contact sensing, contact maintenance, robotic catheter control, and/or mapping. Console 300 can be coupled to the ablation catheter 100 in one or more of a variety of manners, such as by at least one conduit 125. The conduit 125 can be or include one or more communication paths (e.g. one or more wires or optical fibers) for the transmission of electrical and/or optical signals, as examples.

In FIG. 2, a set of functional elements 119 is shown at the distal end of the ablation catheter 100, as part of the force maintenance assembly 150. Similarly, a set of functional elements 129 is shown at the proximal end of the catheter 100, and at the handle 120. The functional elements can be coupled together via a communication path 125', such as one or more wires, fibers, and/or conductive traces, as examples.

The functional elements 119 can be contact maintaining elements, e.g., elements configured to cause the ablation element 130 to maintain contact with tissue, once such contact is achieved. The contact maintaining elements can be located at the distal end of ablation catheter 100, such as one or both of functional elements 119.

The contact maintaining functional elements 119 can be any one or more of a variety of functional elements, such as hooks or barbs, cryogenic elements to which the tissue sticks, and/or a vacuum that pulls the tissue and the ablation element 130 into contact, each of which preferably maintains the contact during ablation. Once ablation is complete, the contact maintaining functional elements 119 can be released or otherwise disengaged from the tissue.

Control 121 can be used to steer the ablation catheter 100 and/or to control the contact maintaining functional elements 119. In some embodiments, one or more of the functional elements 129 can be used to control one or more of the functional elements 119, such as by causing the functional elements 119 (as contact maintaining elements) to selectively engage and disengage the tissue, which can be accomplished using communication path 125'.

In some embodiments, functional element 129 of handle 120 comprise a transducer configured to alert the user and/or otherwise indicate to the user the status of one or more components of system 10. For example, functional element can comprise a light source, and the housing of handle 120 can comprise an at least partially translucent housing, such that the light source illuminates the housing to inform the user of an issue and/or the state of system 10 (e.g. a state in which energy is or is not being delivered, and/or a state in which sufficient contact with tissue is or is not being achieved). In some embodiments, the intensity of the light can be adjusted to correspond to one or more variable conditions, such as the proximity of ablation element 130 to tissue, amount of compression of force maintenance assembly 150, level of pressure exerted by catheter 100 on tissue, and combinations of one or more of these. In some embodiments, varying the color of the light can be used to represent different information. Additionally or alternatively, blinking or other modulation of the light can be used to indicate any variation of one or more states of system 10.

In some embodiments, functional element 129 comprises a haptic transducer that can be configured to inform the user of the status of one or more components of system 10. One or more characteristics (outputs) of a haptic signal can be modified to vary the status message delivered to the user, such as one or more characteristics selected from the group consisting of: frequency of the haptic signal; pulse width of the haptic signal; intensity of the haptic signal; pattern of the haptic signal, such as a Morse code pattern or other code pattern; and combinations of one or more of these.

In the embodiment of FIG. 2, the ablation catheter 100 can also include contact sensing sensors or other contacting sensing elements, contact sensing elements 158. That is, contact sensors can take the form of functional elements configured to sense contact, as contact sensing elements 158. Contact of the ablation element 130 to the tissue can be sensed using the contact sensing element 158. In various embodiments, contact sensing can be used to give a yes/no answer (contact/no contact) indication of whether or not the tip of the electrode, e.g., ablation element 130, is in contact with targeted tissue. Contact sensing can also be used to quantify contact amount and/or assess quality of contact. As an example, sensed electrical characteristics, such as magnitude and/or frequency of a sensed electrical signal, can be related to different levels of contact, e.g., wherein different levels are associated with different measures of magnitude and/or frequency of a sensed electrical signal.

In some embodiments, contact sensing elements 158 can be configured to produce a signal (e.g. a signal received by console 300 of system 10), correlating to the proximity and/or orientation of ablation catheter 100 to an object within the cardiac chamber and/or on the surface of the cardiac chamber. For example, the signal can comprise a voltage signal, such as a voltage signal with a resolution (e.g. a resolution indicating a measurable change in proximity and/or orientation) of at least 0.010 mV, or at least 0.015 mV, per 0.1 mm change in distance between the sensing element 158 and the object and/or surface. In some embodiments, the system is configured to detect a surface and/or an object within at least 8 mm, within at least 10 mm and/or within at least 12 mm of one or more sensing elements 158.

Contact sensing elements 158 can be included at the distal end of the ablation catheter 100, as an example. Contact sensing signals from these sensing elements 158 can be communicated to the console 300 via the communication path 125' and conduit 125. As an example, signals indicating sensed contact can be processed by a signal processing module of the console 300, such as a functional module 342 (e.g. a module comprising signal processing circuitry, one or more algorithms, and/or other components configured to receive, process and/or analyze a signal), force maintenance module 340, processor 330, etc.

In various embodiments, contact sensing elements 158 can be selected from a group comprising: piezoelectric strain sensor; piezoelectric acoustic sensor; impedance contact sensor; electrode contact sensor; pressure sensor (irrigation contact sensor), as examples.

As an example, a piezoelectric contact sensor can be arranged and configured to function as a strain/voltage sensor. When under a compressive load, piezoelectric materials generate a charge. A piezo contact sensor would compress when in contact with tissue, and generate a voltage. Multiple piezo sensors can give directional information and/or orientation information. For example, processors of console 300 can be configured to differentially compare voltages of multiple sensors to determine orientation information.

As another example, a piezoelectric contact sensor can be arranged and configured to function as a sensor that senses changes in acoustic impedance. Baseline acoustic impedance between two elements can be measured. Impedance would change when one or more of the elements is in contact with tissue. Changes in acoustic impedance would indicate a change in contact (e.g. a change in contact force or a change from no contact to some contact).

As another example, the contact sensing elements 158 can be arranged and configured to function as an impedance-based contact sensor. Electrode impedance changes based on tissue contact can be measured. Greater contact pressure causes a resulting greater drop in impedance. Therefore, measured impedance goes down with increased contact. Differences in measured impedances could be used to show relative contact changes (e.g. changes to contact force and/or pressure).

As another example, the contact sensing elements 158 can be arranged and configured to function as an electrode-based (bipolar) contact sensor. One or more electrode pairs (e.g. multiple multiplexed pairs) with a signal between each pair, would be sensitive to tissue contact and/or mechanical stimulus. Signal changes between electrodes in an electrode pair can be monitored and used to detect and determine contact and/or mechanical stimulus. Mechanical stimulus sensitivity is independent of conductivity of the surface providing stimulation. In some embodiments, system 10 can apply a signal between any electrode pair (e.g. any electrode pair of a catheter or other patient inserted device), to measure tissue contact and/or mechanical stimulus, without the need for additional components (e.g. on the device) to perform the measurement. This electrode-based contact sensor arrangement can also be used to detect proximity, as well as an "angle of attack" (orientation between an ablation element or other catheter component and a tissue surface), by creating multiple electric fields and measuring the difference between the multiple fields.

In some embodiments, mapping electrodes 135 and 135a are configured as sensing elements 158. In some embodiments, ablation catheter 100 comprises additional electrodes configured as sensing elements 158, such as a total of 3, 4, 5 or more mapping electrodes 135. System 10 can be configured to transmit (source) a signal from a first mapping electrode 135 and receive (sink) the signal by a second mapping electrode 135a, the signal used to determine the proximity and/or orientation of ablation catheter 100 to an object, surface, and/or boundary within the cardiac chamber. The signal can comprise an applied voltage and/or a sourced current, such as a voltage or current comprising a frequency between 1 kHz and 1 MHz, such as between 10 kHz and 100 kHz, such as 20 kHz. The signal creates an electrical field between the source and sink electrodes, which can be measured by one or more additional sensors of system 10, such as by one or more electrodes of ablation catheter 100.

The spatial distribution of current flow through the blood or tissue surrounding the source and sink electrodes establishes a spatially-varying potential field that can be measured at the location of any electrodes on the ablation catheter 100 (or another device within the potential field) as a voltage, relative to a reference electrode (e.g. a reference patch electrode). The relative position or spacing of the electrodes within the potential field can be determined from the voltage measurement at the electrodes. In some embodiments, the spacing between any two or more electrodes within the potential field can be measured, such as to determine the compression distance of an element of the force maintenance assembly 150, such as when a first electrode is positioned on the shaft 110 of ablation catheter 100 and a second electrode is positioned on or near the tip of ablation catheter 100. The change in spacing as a function of time can be used to determine the stability of engagement of the force maintenance assembly, which can correlate to the stability of tissue contact. The shape and/or spatial structure of the potential field is determined by the boundary conditions established by the tissue or other variations in impedance in the local environment. Accordingly, the spatial distribution of current flow can also vary as a function of the proximity and/or orientation of structures and/or boundaries of differing characteristic impedance near the source and sink electrodes. The shape and/or spatial structure of the field can be derived from measurements at any electrode on the ablation catheter 100 (or any device within the field) using an algorithm such as a fitting function. The electrodes selected to source and sink the current can be alternated, modulated and/or otherwise multiplexed between different pairs of electrodes on the ablation catheter 100 to obtain alternate measures of the effect that the boundary conditions of the local environment have on the shape and spatial structure of the field. When current is sourced and/or sinked from an alternate pair of electrodes, an alternate potential field is established and alternate measurements from any electrodes within the field can be measured. If one or more alternate field configurations are established and measured in a duration of time short enough that the local environment (relative position and/or orientation of boundary conditions) remains generally the same (e.g. a duration less than 1 second, such less than 100 ms or less than 10 ms), the set of multiplexed, alternate measurements can be used to establish a system of equations for which an algorithm can be used to determine and/or reconstruct the state of the boundary conditions for the duration of time. In this manner, the proximity and orientation of the ablation catheter 100 to the tissue can be determined. In some embodiments, at least 3 electrodes are used as described herein to determine the boundary conditions, such as at least 4 or at least 5 electrodes, to support at least 1 alternate source/sink configuration, such as at least 2, at least 6, at least 10 alternate configurations used to determine the complexity of the boundary conditions.

As another example, the contact sensing elements 158 can comprise a flow sensor (e.g. an ultrasonic flow sensor or other flow sensor) arranged and configured to function as an irrigation flow sensor, with a pressure sensor installed "post pump" (e.g. between the source of irrigation fluid and an irrigation port outlet of the catheter). When irrigation channels are blocked (e.g., by tissue contact), pressure goes up indicating such contact.

Figure 3A:
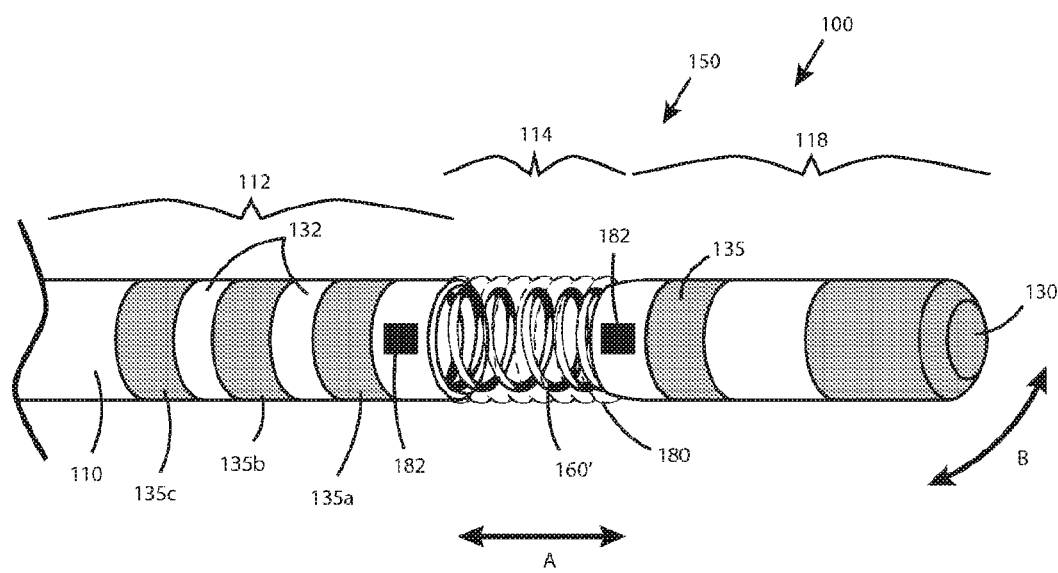
FIGS. 3A-3C illustrate a set of perspective views of a distal portion of an ablation catheter comprising a force maintenance assembly that includes a spring, consistent with the present inventive concepts.
Figure 3B:
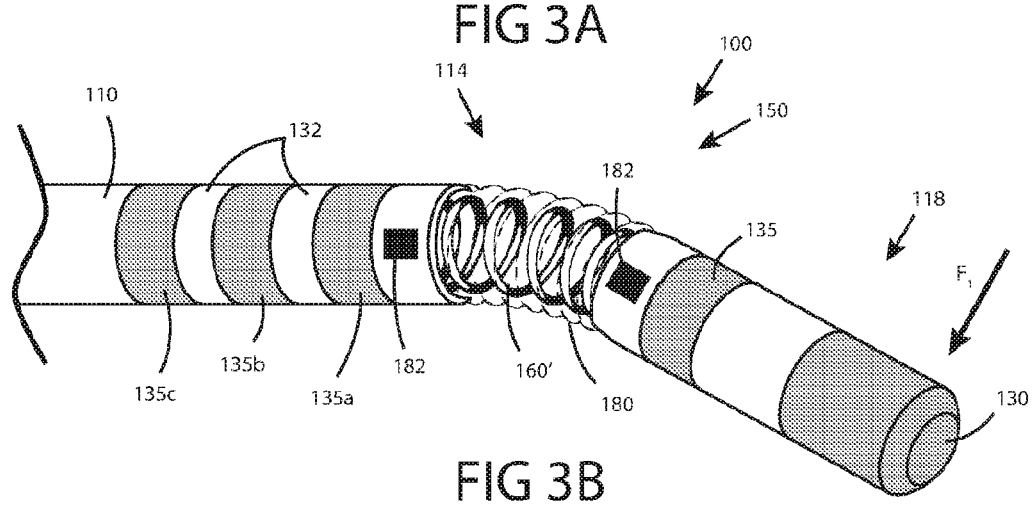
Figure 3C:
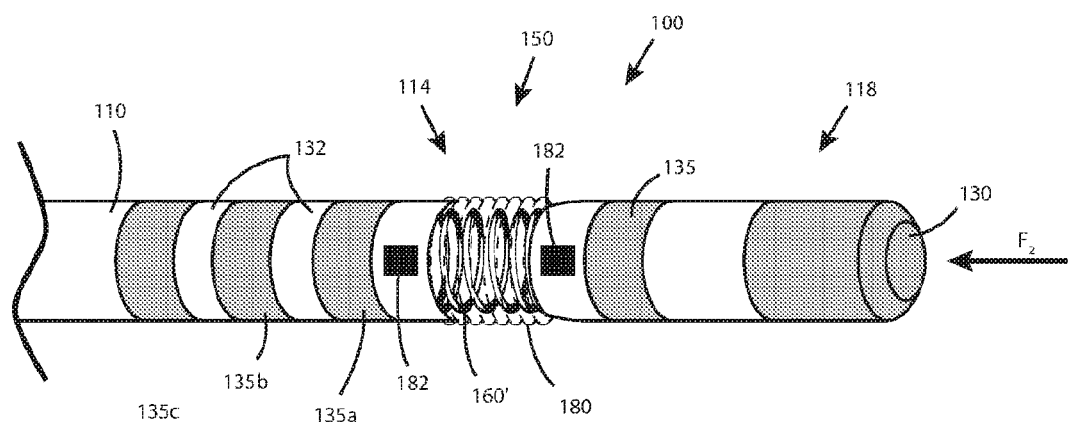

Referring now to FIGS. 3A-3C, a set of perspective views of a distal portion of an ablation catheter comprising a force maintenance assembly 150 is provided, consistent with the present inventive concept. In various embodiments, the force maintenance assembly 150 can include a constant force spring or other device that provides a constant force. Such constant force spring or other devices can advantageously provide constant force during ablation, for example.

FIG. 3A shows an embodiment of a force maintenance assembly 150. Generally, this portion of the ablation catheter 100 includes a shaft 110 distal portion 112, the force maintenance assembly 150, which includes a flexible/compressible portion 114, and a "floating tip portion", floating tip portion 118. The floating tip portion 118 is the distal-most portion of the ablation catheter 100 and includes the ablation element 130, in this embodiment. One or more mapping electrodes 135 and 135a,b,c can also be included, which can be separated from the ablation element 130, and each other, by one or more electrical isolators 132.

The flexible/compressible portion 114 of the force maintenance assembly 150 enables a range of motion of the floating tip portion 118 with respect to the shaft 110. In some embodiments, this range of motion can be limited to a linear motion that is substantially coaxial with the shaft 110, as indicated by arrow "A". In other embodiments, the range of motion can include angular motion relative to the shaft 110, such that the floating tip portion 118 can be rotated off-axis with respect to the shaft 110, as indicated by arrow "B". In this embodiment, the range of motion preferably includes both linear and angular motion of the floating tip portion 118 with respect to the shaft 110.

In FIG. 3A, the flexible/compressible portion 114 comprises a force maintenance element 160 that includes at least one spring element 160' (e.g. one or more springs or other spring elements). Spring element 160' can comprise Nitinol and/or other shaped memory metal and/or polymer. In some embodiments, heating, cooling and/or an electric current (e.g. an electric current configured to increase the temperature of spring element 160') is applied to a nitinol and/or other shaped memory material to adjust the forces of spring element 160'. In some embodiments, spring element 160' comprises one or more materials selected from the group consisting of: Nitinol; a super elastic polymer; a polymer; and combinations thereof. Spring element 160' can comprise a constant force spring. Spring element 160' can comprise multiple spring elements comprising polymers of varying durometer (e.g. in series or parallel within a catheter shaft). Spring element 160' can comprise a resilient biased bellows.

Spring element 160' is an example of a functional element 119 that can be compressible and/or flexible. For example, the spring element 160' can be a coil spring biased in an uncompressed state. Spring element 160' can comprise a metal shaft, piston or other tube with one or more laser cuts that configure the tube as a spring. A spring constant of spring element 160' can be chosen to enable compression of the spring in response to a force experienced by the floating tip portion 118 that does not compromise or damage the tissue against which the ablation element 130 is in contact. The flexible/compressible portion 114 of the shaft 110 can, therefore, be configured to cause the ablation element 130 to remain in contact with the tissue being targeted (e.g. for ablation) over a range of motion enabled by the spring element 160', whether the motion is caused by movement of the shaft 110, the tissue, or both.

In this embodiment, spring element 160' is encased by a bellows, bellows 180. The bellows 180 can prevent ingress of fluids and other materials into the shaft 110 via the flexible/compressible portion 114. The bellows 180 can also help maintain a vacuum within the catheter shaft 110, if a vacuum is used. The bellows 180 can also help prevent egress of fluids or materials from inside the shaft 110 into the cardiac chamber, for example hydraulic or pneumatic fluids.

For example, the bellows 180 surrounding at least a portion of force maintenance assembly 150 (e.g. surrounding one or more moving components of force maintenance assembly 150) can shield them from biological surroundings (e.g. biological contaminants). In some embodiments, the bellows 180 could surround the spring element 160', such as a spring element 160' comprising a metal shaft, piston or other tube (e.g. a tube with laser cuts that configure the tube as a spring). In some embodiments, "micro bellows" could be used.

In various embodiments, the bellows 180 are constructed from a thin walled elastomer, thermoplastic polyurethane (TPU), thermoplastic vulcanizate (TPV), thermoplastic elastomers (TPE), and the like, which can be configured to prevent the bellows 180 from adding significant stiffness to catheter 100 and/or floating tip portion 118. In some embodiments, the bellows 180 can take the form of a pre-stretched extrusion (e.g. an elastomeric extrusion) that will not "bunch" when compressed.

Generally, the bellows 180 can prevent stiffness in the catheter tip, or floating tip portion 118 of the shaft 110. In some embodiments, the bellows 180 can also be configured to add a spring force. In such cases, the spring force of the bellows 180 can complement that of the spring force of the spring element 160' or other similar force maintenance element 160. In some embodiments, the spring force of the bellows 180 can be the sole or primary force maintenance component of the force maintenance assembly 150.

FIG. 3B shows an embodiment where the floating tip portion 118 has been rotated or deflected off axis with respect to the shaft 110, as a result of an applied force $F_1$ shown. The flexible/compressible portion 114 enables such motion to occur. Such off-axis rotational freedom of movement can help maintain the ablation element 130 in contact with cardiac tissue during an ablation procedure, as an example. Such contact maintenance is further enhanced by the compressible nature of the flexible/compressible portion 114 of the shaft.

FIG. 3C shows an embodiment where the floating tip portion 118 remains coaxial with the shaft 110 while the flexible/compressible portion 114 and bellows 180 are compressed to a fully compressed or semi-compressed state, as a result of an applied force $F_2$ shown.

In each of FIGS. 3A-3C, a pair of magnetic elements 182 is shown, one disposed on each side of the flexible/compressible portion of the shaft. The magnetic elements 182 can be configured to repel each other. The repellant force of the magnets 182 in combination with the spring force of the spring 160' can be chosen to enable the flexible/compressible portion 114 to keep the force exerted by the floating tip portion 118 constant or substantially constant. In the embodiment shown, a coil spring is used as a spring element 160'.

In this magnet-spring combination, magnets 182 positioned with opposing polarities towards each other assist/resist the spring force of the spring 160'. As the spring 160' compresses (spring force goes up), the magnets 182 repel each other, such as to keep the overall relatively force constant.

In some embodiments, the magnets 182 could also help avoid or limit transverse deflection of the floating tip portion 118, by providing cooperating magnetic fields that bias the floating tip portion toward a "straight" position.

In some alternate embodiments, the force maintenance assembly 150 could include magnets, without the use of a spring (e.g. spring element 160' comprises one, two or more magnets without the inclusion of a spring). The magnets can be used to create a spring-like force between the floating tip portion 118 and the catheter shaft 110.

Figure 3D:
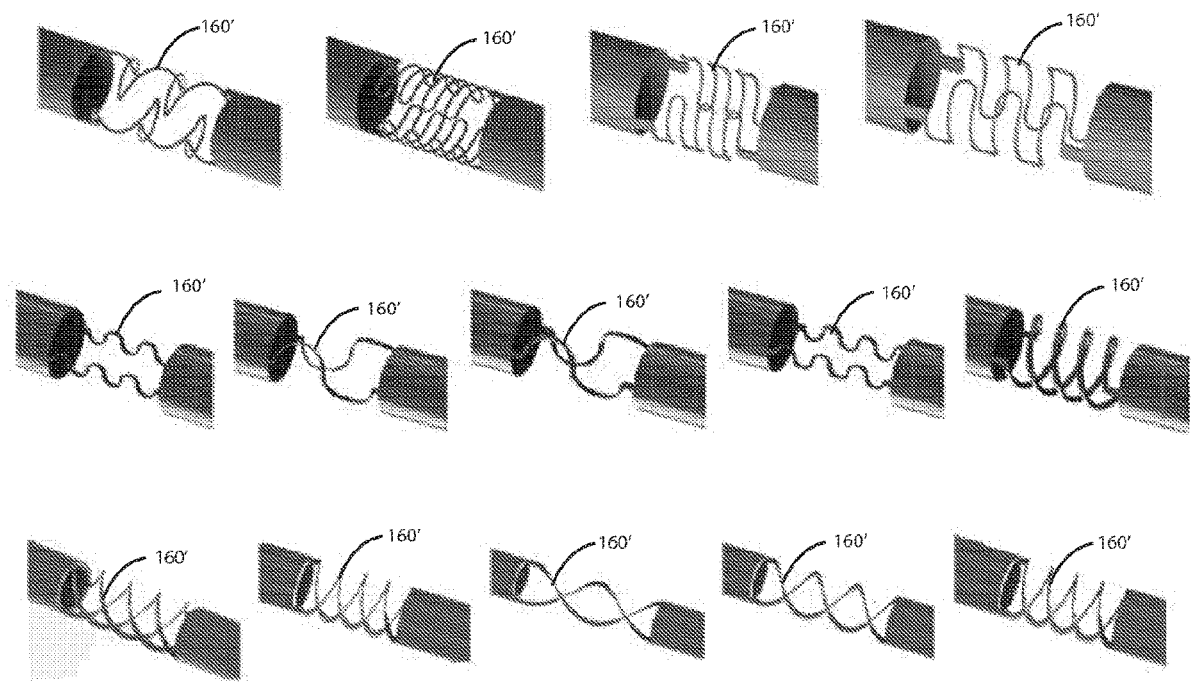
FIG. 3D provides a set of perspective views showing a plurality of embodiments of springs that could be used in the distal portion of an ablation catheter comprising a force maintenance assembly, consistent with the present inventive concepts.

Spring element 160' can comprise one, two or more different types of springs. FIG. 3D shows fourteen different embodiments of spring element 160', and one or more of these could be included in the flexible/compressible portion 114 and/or force maintenance assembly 150. Spring element 160' shapes preferably minimize outer diameter (OD) growth when compressed. Use of custom "spring geometries," as in the examples of FIG. 3D, that provide a force range with a maximum force (e.g. from "any angle"), could be used, wherein:

ContactForce=SpringForceMAX cos(contact angle)
  <SpringForceMAX

Figure 4A:
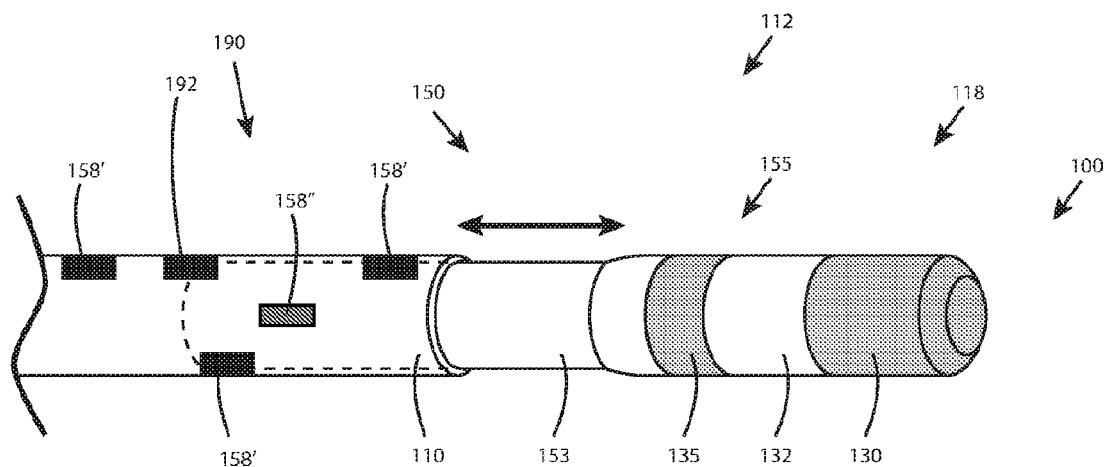
FIGS. 4A-4B illustrate a set of perspective views of a distal portion of an ablation catheter comprising a force maintenance assembly that includes a displacement sensor, consistent with the present inventive concepts.
Figure 4B:
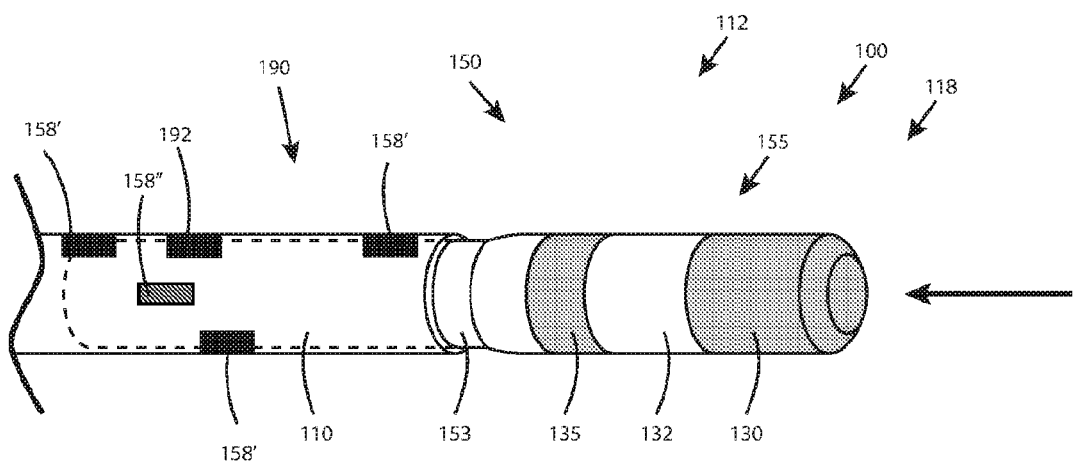

FIGS. 4A-4B illustrate a set of perspective views of an embodiment of a distal portion 112 of an ablation catheter 100 comprising a force maintenance assembly 150 that includes a displacement sensor 190, consistent with the present inventive concepts.

Referring now to FIG. 4A, a portion of the shaft 110 is shown with the force maintenance assembly 150 disposed between the floating tip portion 118 (e.g. a tubular segment that slides within the distal end of shaft 110) and the shaft 110. In this embodiment, the force maintenance assembly 150 allows linear movement of the floating tip portion 118 with respect to the shaft 110. Furthermore, the linear movement can be coaxial with the shaft 110, as is shown in the embodiment of FIGS. 4A and 4B.

As in other embodiments, the floating tip portion 118 includes an ablation element 130 at its distal end or tip. One or more mapping electrodes 135 can also be included on the floating tip portion 118 and/or shaft 110. The mapping electrodes 135 can be separated from the ablation element 130 and from each other by one or more electrical isolators 132.

In particular, in this embodiment, the force maintenance assembly 150 includes a piston 155 having at least a portion that travels linearly in and out of the shaft 110, indicated by the double arrow in FIG. 4A. The piston 155 includes an outer shaft 153 that is increasingly exposed as the force maintenance assembly 150 causes the floating tip portion 118 to travel outward and away from the shaft 110, via piston 155, toward its extended state shown in FIG. 4A. That is, the force maintenance assembly 150 can bias the floating tip portion 118 into an extended state.

A force applied to the floating tip portion 118, as shown in FIG. 4B, can cause the floating tip portion 118 to travel toward the shaft 110, in a compressed or semi-compressed state enabled by the force maintenance assembly 150. When such pressure or force is diminished or removed, the biased force maintenance assembly 150 returns the floating tip portion 118 to its extended (non-compressed) state as shown in FIG. 4A.

In some embodiments, the displacement sensor 190 can include one or more sensing elements 158 arranged and configured to determine whether or not the floating tip portion 118 has been displaced relative to the shaft 110, such as to provide a "yes" or "no" indication. Additionally or alternatively, the displacement sensor 190 can include one or more sensing elements 158 arranged and configured to determine an amount of linear travel (e.g. a displacement measurement) and/or a linear position (e.g. an absolution position measurement) of the piston 155 and, therefore, the floating tip portion 118. In this embodiment, the displacement sensor 190 includes one or more sensing elements 158' disposed on and/or in the shaft 110, and one or more sensing elements 158" disposed on and/or in the force maintenance assembly 150 and/or piston 155 thereof. That is, in FIGS. 4A and 4B, a plurality of stationary sensing elements 158' are dispersed along a length of the shaft 110 and at least one movable sensing element 158" is disposed on and/or in the piston 155 of the floating tip portion 118. As the piston 155 travels within the shaft 110, the stationary sensing elements 158' detect the relative position of the at least one movable sensing element 158" on the piston 155, such as to enable a determination of a travel distance of the floating tip portion 118 relative to the shaft 110. Determining a travel distance of the floating tip portion 118, or the piston 155 thereof, enables determination of a position or location of the ablation element 130.

In various embodiments, the displacement sensor 190 can be or include one or more sensors selected from a group consisting of: capacitive sensor; linear potentiometer; linear variable differential transformer (LVDT); Hall effect sensor; tactile sensor; optical sensor; load cell; and combinations thereof.

As an example, as a capacitive sensor as a portion of floating tip portion 118 moves between capacitive elements, changes in capacitance proportional to distance are experienced and can be sensed and recorded. As another example, as a potentiometer (e.g. a linear potentiometer), linear displacement distance can be determined by connecting the movable floating tip portion 118 to a potentiometer's wiper/slide element. As another example, as a linear variable differential transformer (LVDT), electromagnetic coupling can be used between stationary sensing elements 158' on the shaft and movable sensing elements 158" on the floating tip portion (or piston 155 thereof) to determine linear displacement. As a Hall effect sensor, the movable floating tip portion 118 can include a magnetic portion that moves relative to a Hall effect sensing element 158' in the shaft, for example. As a tactile sensor, the movable floating tip portion 118 can include a sensing element or elements 158" that contacts tactile sensing elements 158' within catheter shaft 110. As an optical sensor (see also FIG. 6) a light source, tapered slit, and photodetector could be utilized as a displacement sensor 190 (see below) where an amount of detected light correlates to linear displacement of the floating tip portion 118 relative to the shaft 110. As a load cell sensor, a load cell in the catheter handle 120 can be attached to the movable floating tip portion 118 and detect displacement distance based on a translation of the floating tip portion 118 relative to the shaft 110.

As will be appreciated by those skilled in the art, other forms of linear displacement assemblies, sensors, and elements could be used to detect or otherwise determine a linear displacement of the movable floating tip portion 118 relative to the shaft 110. For example, if the shaft 110 included a functional element in the form of at least one electrode, a displacement of floating tip portion 118 could be measured via a change in potential between an electrode, e.g., mapping electrode 135, on the floating tip portion 118 (e.g., a mapping electrode 135 or ablation element 130) and the functional element (i.e., at least one electrode) on the shaft 110. That is, a bipole "pair" could be established between at least one shaft electrode and at least one floating tip portion electrode where changes in distances between the electrodes of the pair result in changes in delivered and/or received signals from the pair of electrodes (e.g. changes in potentials between the electrode pair).

In some embodiments, movable sensing elements 158" can comprise one or more ferrite "strips". Multiple ferrite strips along piston 155 could cause a measured inductance to change in a "step" like manner, and the measurement could be used to increase effective distance measurement of the system. Additionally, or alternatively, movable sensing element 158" can comprise magnetic tape configured to create a unique local magnetic field along piston 155. In some embodiments, at least a portion of piston 155 can comprise a magnetic material, such as a mu-metal or other ferrous material.

As depicted in the example of FIG. 4A, the shaft 110 could include a locking element 192 configured to lock (e.g. temporarily lock) the floating tip portion 118 in a fixed position relative to the shaft 110. The locking element 192 can be used to lock the catheter 100 to behave in "standard" mode, e.g., without force maintenance, force sensing, and/or force limiting. The locking element 192 can be configured to lock the floating tip portion 118 in a fixed position relative to the shaft 110, by mechanical, electromechanical, magnetic, vacuum, and/or other structures and approaches. The locking element 192 can be controlled by a control 121 at the handle 120, through a user interface on a computer display (e.g. a user interface of console 300), and/or by other structures and approaches.

In various embodiments, multiple sensors (as functional elements) can be used to add further constraint to the system. As an example, an inductive based system with multiple coils could measure displacement, angular displacement, overall position and orientation of movable portion (with functional elements—coils) relative to the shaft (with functional elements—coils).

As few as three sensors can be used to detect the lateral components of force. A sensor at the distal end can be used to measure the axial component of force. The tip position and stiffness can also be tuned electromagnetically via the coils. By forcing the coils closer or further apart with an induced signal, the tip can be actuated via a feedback network to provide force maintenance.

In various embodiments, multiple sensors (as functional elements) can be used to measure resonant frequency change in induction base system, such as by using IQ demodulation. This approach could offer better results than measuring "raw" voltages. A coil based system could include: coil in catheter shaft 110 and "plunger," which can have ferrite tape wrapped around the plunger. In such a system, movement of the plunger would change the self-inductance of the coil.

Figure 5A:
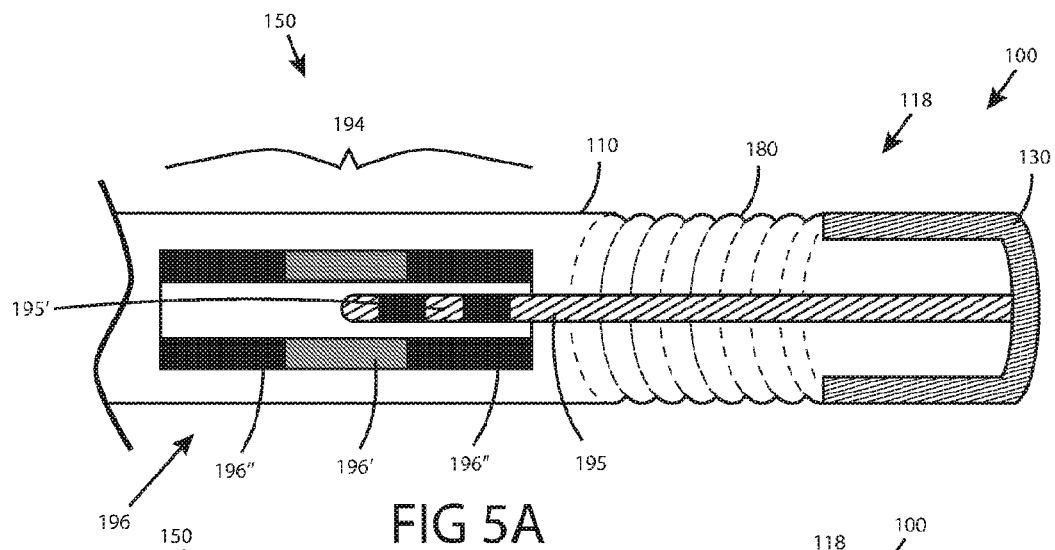
FIGS. 5A-5C illustrate a set of perspective views of a distal portion of an ablation catheter comprising a force maintenance assembly that includes an inductive coil-based displacement sensor, consistent with the present inventive concepts.
Figure 5B:
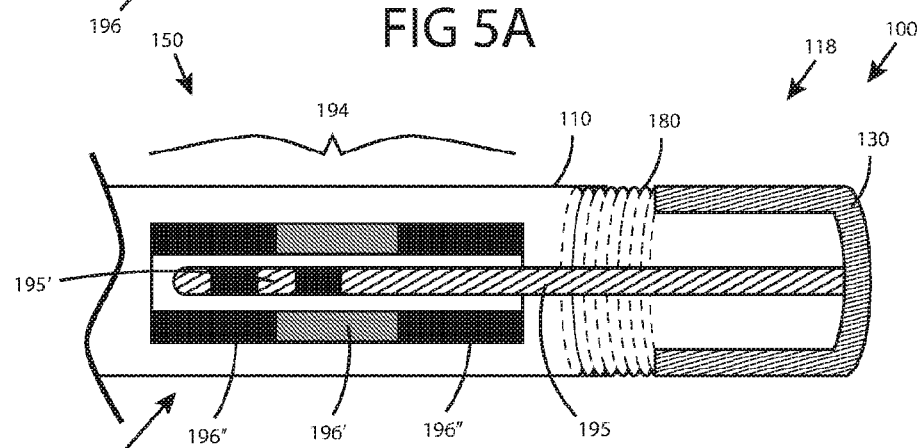
Figure 5C:
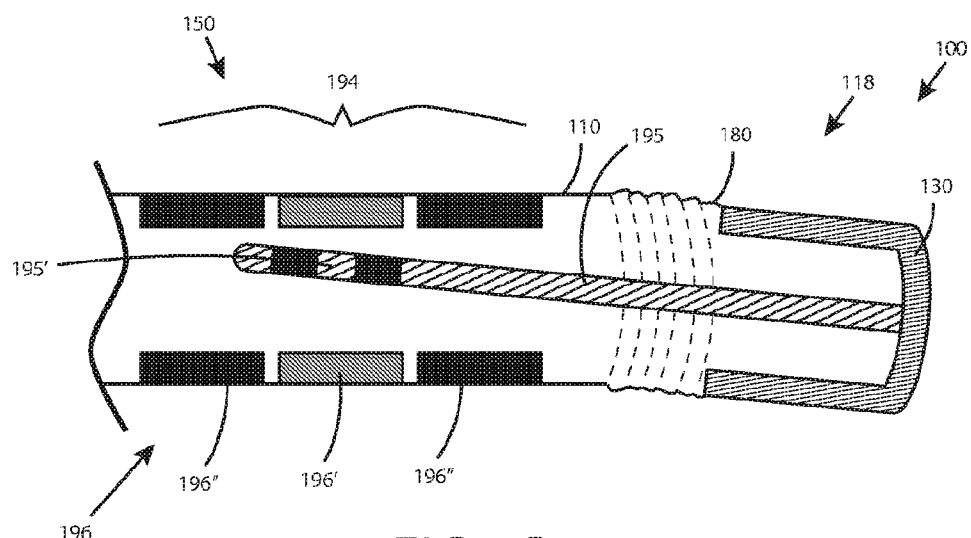

FIGS. 5A-5C illustrate a set of perspective views of a distal portion of an ablation catheter comprising a force maintenance assembly that includes an inductive coil-based displacement sensor, consistent with the present inventive concepts.

In this embodiment, the inductive coil-based displacement sensor includes a linear variable differential transformer (LVDT) structure 194 used to measure linear displacement of the floating tip portion 118 of the catheter 100. Bellows 180 can be designed as a shock absorber and/or a spring element surrounding the LVDT 194. The known spring force (of the bellows) and displacement (from LVDT) could be used to measure or otherwise determine a force applied to the floating tip portion 118 or ablation element 130 of the catheter 100.

An LVDT is an electromechanical transducer that can convert the rectilinear motion of an object to which it is coupled mechanically into a corresponding electrical signal (e.g. a signal with a voltage that changes in correlation to the movement). As shown in FIGS. 5A and 5B, the LVDT 194 of the present invention includes an internal rod 195 which can extend from the floating tip portion 118 back toward the relatively stationary catheter shaft 110. A proximal end of the rod, closest to the handle 120, can be arranged to move axially within a sensing element 196. The proximal end of the rod includes a magnetically permeable material or "core" 195'. In this embodiment, the sensing element 196 is a tubular element having a magnetic shell within which is disposed a plurality of windings that includes a primary winding 196' and two secondary windings 196" formed around a hollow bore. The core 195' is free to move axially within the hollow bore of the tubular sensing element 196.

In operation, the LVDT's primary winding 196' is energized by an alternating current of appropriate amplitude and frequency. The LVDT's electrical output signal is the differential AC voltage between the two secondary windings 196", which varies with the axial position of the core 195' within the LVDT coil. The AC output voltage can be measured to determine linear displacement of the floating tip portion 118 relative to the shaft 110. Alternatively or additionally, the AC output voltage can be converted (e.g. by suitable electronic circuitry) to a DC voltage and/or current, such as a DC voltage or current that is more convenient to use than an AC voltage for determining linear displacement of the floating tip portion 118 relative to the shaft 110.

In alternative embodiments, a capacitive sensor could be used, e.g., instead of LVDT, to determine displacement and/or pressure of the floating tip portion 118 or ablation element 130 of the catheter 100, where a change in capacitance correlates to the displacement.

In still other embodiments, a spring could be used to measure position or displacement, such as a spring also configured as an inductor to measure displacement, where a change in inductance correlates to the displacement (e.g. a change in inductance measured using synchronous demodulation).

Referring to FIG. 5C, an embodiment of a distal portion of an ablation catheter comprising a force maintenance assembly that includes an LVDT displacement sensor is shown. In this embodiment, the hollow bore of the tubular sensing element 196 is sufficiently wide to allow some angular movement of the rod 195 therein. Therefore, while the embodiment of FIGS. 5A and 5B are more limited to a linear displacement of the floating tip portion 118, the embodiment of FIG. 5C also allows for some angular displacement of floating tip portion 118. The bellows 180 coupling the floating tip portion 118 further allows both linear and angular displacement of the rod 195 and, therefore, the floating tip portion 118 with respect to the shaft 110.

Figure 6A:
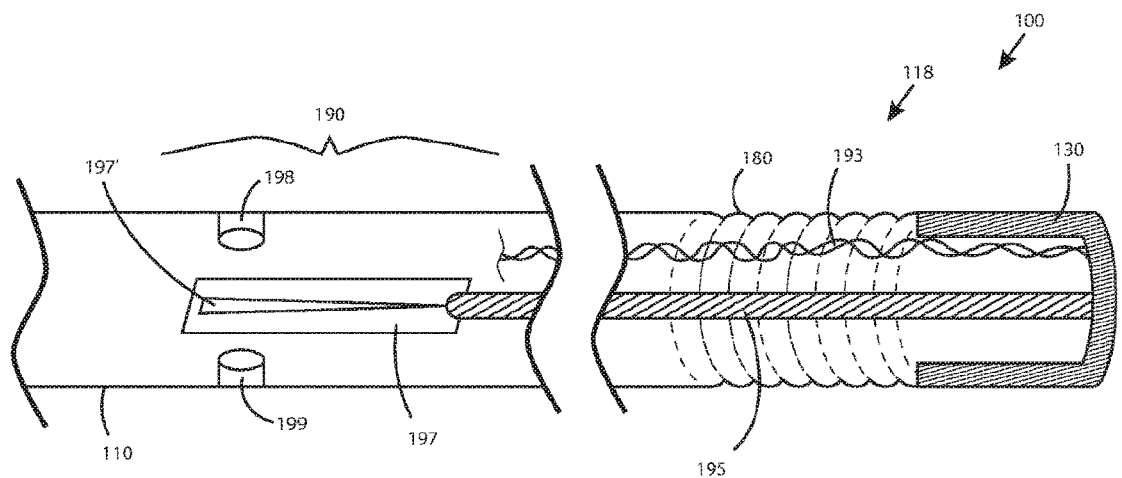
FIGS. 6A-6B illustrate a set of perspective views of a distal portion of an ablation catheter comprising a force maintenance assembly that includes an optical displacement sensor, consistent with the present inventive concepts.
Figure 6B:
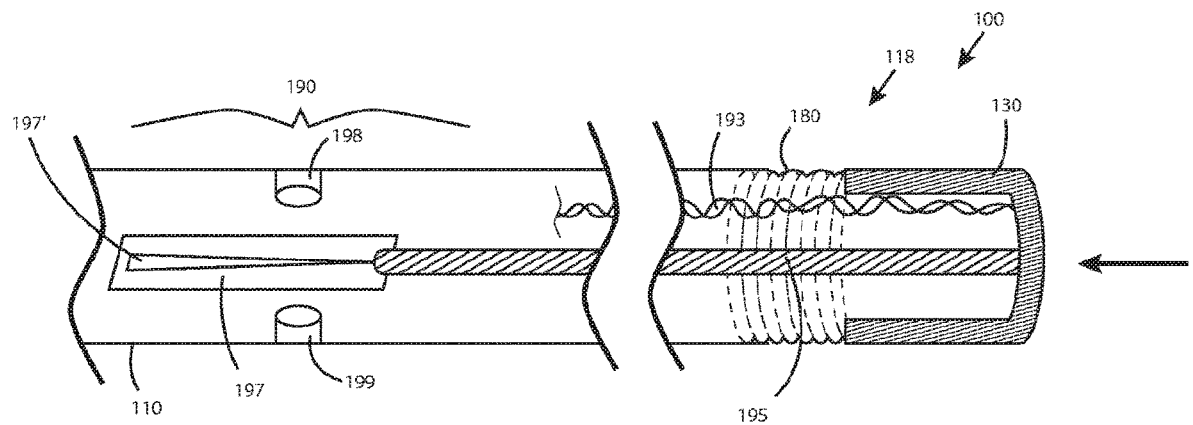

FIGS. 6A-6B illustrate a set of perspective views of a distal portion of an ablation catheter comprising a force maintenance assembly 150 that includes an optical displacement sensor, consistent with the present inventive concepts. FIG. 6A shows the floating tip portion 118 in an extended or uncompressed state, while FIG. 6B shows the floating tip portion 118 in a compressed state.

The optical displacement sensor 190 includes a light source 198 and sensor 199 separated within the shaft 110. A movable element 197 with a tapered slit 197' is coupled to the floating tip portion 118. The amount of light that passes through the slit 197' correlates to position of movable element 197 and, therefore, the floating tip portion 118. In some embodiments, when floating tip 118 is in a compressed state a reduced amount of light passes through the slit 197' (as compared to when floating tip 118 is an expanded or uncompressed state). A shaft or rod 195 can couple or connect the movable element 197 to the floating tip portion 118.

The movable element 197, light source 198, and sensor 199 can be disposed at or near the distal end of catheter 100, at a proximal end of the shaft 110, somewhere therebetween, or in the handle 120, as examples.

FIGS. 6A and 6B show wires 193 traveling through the shaft 110 to the distal portion of the catheter 100, and passing thru the compressible section (bellow 180), as being "coiled" or twisted to minimize resistance to compressing from the wires 193. Such wires can be for any of a number of purposes, such as controlling the ablation element 130 at the distal end of the catheter 100, or for passing any number of other signals to the handle 120, console 300, or other functional element. Those skilled in the art will appreciate that such coiled or twisted wires could be implemented in any of the various embodiments where the floating tip portion 118 is movable with respect to the shaft 110, particularly where linear and/or angular displacement between the two is possible (e.g. and the wires 193 need to accommodate the displacement).

Figure 7:
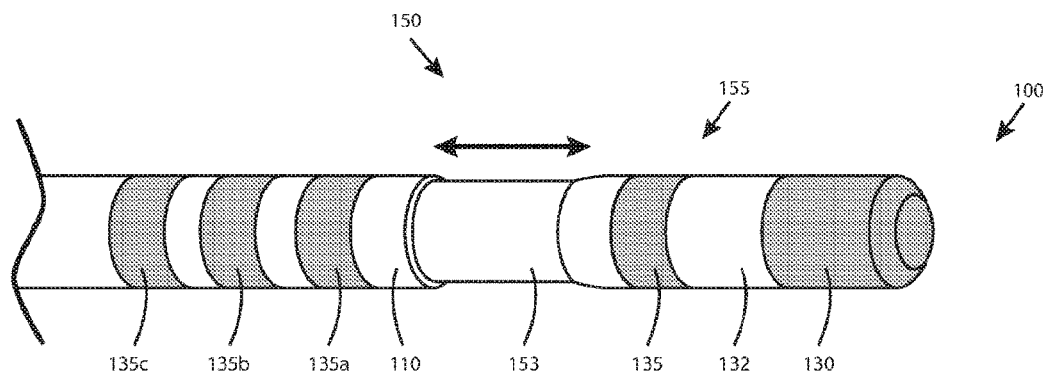
FIG. 7 illustrates a perspective view of a distal portion of an ablation catheter comprising a force maintenance assembly that includes a spring, consistent with the present inventive concepts.

Referring now to FIG. 7, a perspective view of a distal portion of an ablation catheter comprising a force maintenance assembly that includes a spring is illustrated, consistent with the present inventive concepts. Ablation catheter 100 comprises shaft 110 and force maintenance assembly 150, which includes piston 155. Ablation element 130 is positioned on the distal end of piston 155. The distal portion of piston 155 includes a non-conductive separator, electrical isolator 132 and a distal-most ring electrode, mapping electrode 135 shown. Electrical isolator 132 can comprise an electrically non-conductive material, and it can be positioned between ablation element 130 and mapping electrode 135 to electrically isolate the two components. Piston 155 comprises outer shaft 153, and shaft 110 of ablation catheter 100 slidingly receives outer shaft 153 of piston 155.

Ablation catheter 100 can include one or mapping electrodes, such as 135a, 135b, and/or 135c shown positioned on shaft 110.

Figures 7A, 7B:
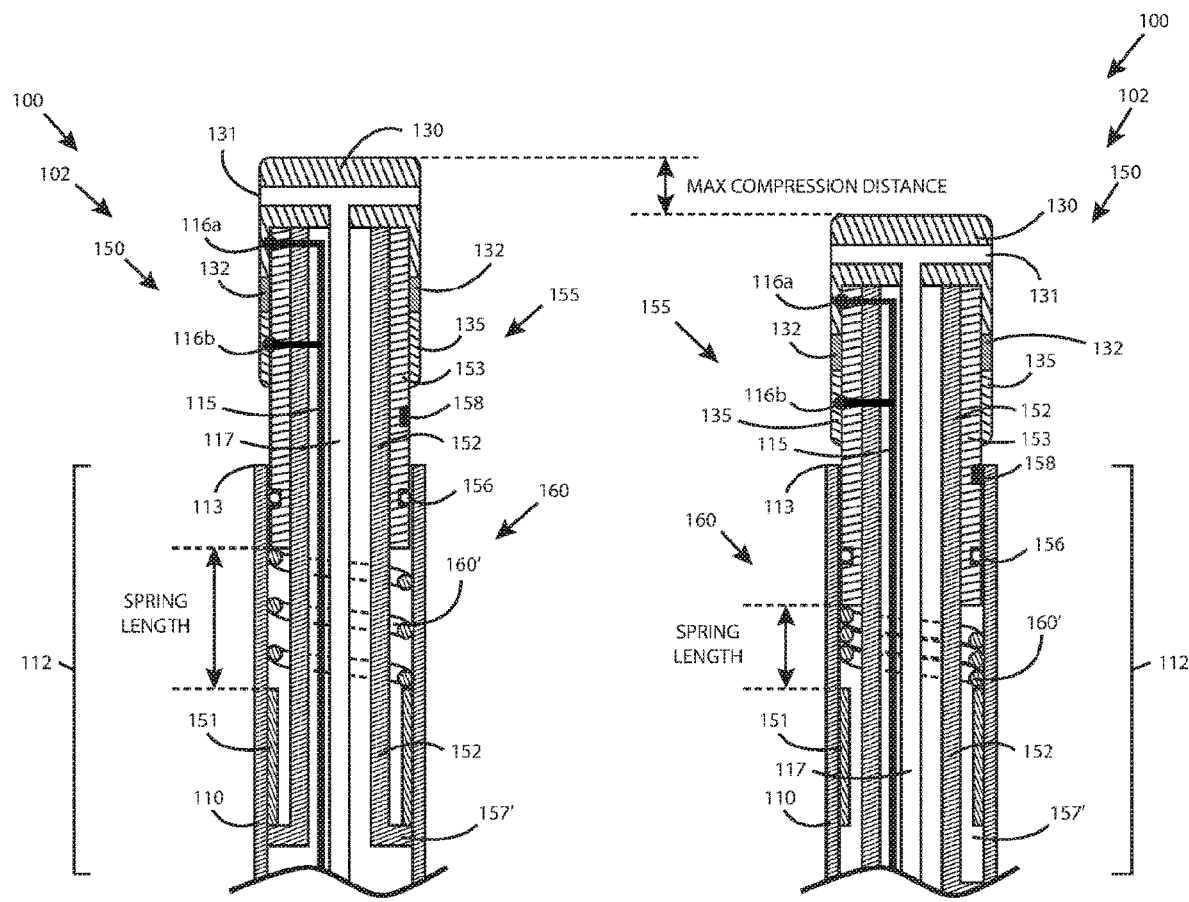
FIGS. 7A and 7B illustrate side sectional views of the distal portion of the ablation catheter of FIG. 7, consistent with the present inventive concepts.

Referring to FIG. 7A, a side sectional view of the distal portion of ablation catheter 100 of FIG. 7 is illustrated with a spring actuated force maintenance assembly 150 shown in a fully extended or uncompressed state. Ablation catheter 100 comprises distal portion 102, shaft 110, ablation element 130, force maintenance assembly 150, and a force maintenance element 160 which comprises a spring, spring 160'. Spring 160' can comprise a constant force spring.

In the embodiments, as shown in FIG. 7A, force maintenance assembly 150 is positioned in distal portion 102 of ablation catheter 100. Force maintenance assembly 150 includes piston 155 comprising inner shaft 152 and outer shaft 153. Inner shaft 152 can include proximal flange 157'. Ablation catheter 100 can comprise one or more conduits, such as conduits 115 shown. Conduits 115 can be configured to provide power, transmit data, and/or receive data, such as power and/or data to and/or from a console connected to ablation catheter 100. Conduits 115 can operably attach to ablation element 130 and one or more mapping electrodes 135, such as via connection points 116a and 116b shown.

Ablation catheter 100 comprises shaft 110 with distal portion 112 and distal end 113. Distal portion 112 slidingly receives piston 155. Shaft 110 includes support element 151 that engages proximal flange 157' of piston 155 to prevent piston 155 from traveling distally beyond the position shown in FIG. 7A (e.g. preventing piston 155 from exiting the distal end 113 of shaft 110). Support element 151 is fixedly attached to the proximal end of spring 160'.

Shaft 110 can include one or more lumens, such as irrigation lumen 117 shown. Ablation catheter 100 can comprise one or more irrigation ports, for example two or more irrigation ports, in distal portion 102, such as irrigation port 131 that can exit ablation element 130 as shown. Additionally or alternatively, irrigation port 131 can comprise one or more ports that exit a portion of piston 155 and/or exit shaft 110 within one or more locations of distal portion 112. System 10 can be configured to deliver fluid to tissue proximate irrigation port 131, such as a cooling fluid delivered prior to, during, and/or after delivery of energy by ablation element 130 (e.g. delivery of RF ablation energy).

Piston 155 is operably attached to spring 160', such that spring 160' resists translation of piston 155 proximally into shaft 110. Support element 151 engages the proximal end of spring 160', preventing spring 160' from traveling proximally into shaft 110.

Outer shaft 153 can include sealing element 156, a component configured to prevent fluid ingress into shaft 110 of ablation catheter 100. Ablation catheter 100 can include sensing elements 158, shown integral to piston 155, to provide a signal indicative of the resulting full and/or partial compression of spring 160'.

Ablation element 130 and mapping electrode 135 move in concert as piston 155 translates relative to shaft 110, maintaining a fixed distance between ablation element 130 and mapping electrode 135. Mapping module 350 of FIG. 1 can be configured to perform bipolar calculations on signals recorded between ablation element 130 and mapping electrode 135, such as when ablation element 130 comprises an electrode. The fixed distance between the ablation element 130 and mapping electrode 135 greatly simplifies the bipolar mapping calculations performed.

Referring additionally to FIG. 7B, a side sectional view of the distal portion of ablation catheter 100 of FIG. 7 is illustrated, with a spring-actuated force maintenance assembly 150 shown in a fully compressed state. The spring length difference shown in FIG. 7A and FIG. 7B (i.e. the expanded distance and the compressed distance, respectively), as a result of compression of spring 160', is indicative of the max compression distance of ablation catheter 100 as described hereabove.

In some embodiments, ablation catheter 100 of FIGS. 7, 7A, and 7B comprise an articulating tip, such as is described herebelow in reference to ablation catheter 100 of FIGS. 8, 8A and 8B.

Referring now to FIG. 8, a perspective view of the distal portion of an ablation catheter comprising a force maintenance assembly including a hydraulic piston is illustrated, consistent with the present inventive concepts. Ablation catheter 100 comprises shaft 110 and force maintenance assembly 150, which includes hydraulic piston 155". Ablation catheter 100 includes ablation element 130, a non-conductive separator, electrical isolator 132, and a ring electrode, mapping electrode 135. Shaft 110 of ablation catheter 100 slidingly receives piston 155". Ablation catheter 100 can include one or more additional mapping electrodes, such as 135a, 135b, and/or 135c shown positioned on shaft 110. In some embodiments, ablation catheter 100 comprises an articulating tip assembly 165, configured to allow the distal portion of ablation catheter 100 to articulate relative to shaft 110, as described herein.

Referring now to FIG. 8A, a side sectional view of the distal portion of ablation catheter 100 of FIG. 8 is illustrated, with a hydraulically actuated force maintenance assembly 150 shown in a fully extended state. Ablation catheter 100 comprises shaft 110, ablation element 130, and force maintenance assembly 150 that includes hydraulic assembly 160". In some embodiments, ablation element 130 comprises a gold and/or a platinum iridium electrode. Ablation element 130 can comprise a length of approximately 3.5 mm, such as a length between 3.0 mm and 4.0 mm.

Shaft 110 can include one or more lumens, such as lumen 117' shown. Ablation catheter 100 can comprise one or more irrigation ports located in catheter distal portion 102, such as irrigation port 131 shown exiting ablation element 130. Additionally or alternatively, irrigation port 131 can comprise one or more ports that exit a portion of piston 155" and/or exit a distal portion 112 of shaft 110. System 10 can be configured to deliver fluid to tissue proximate irrigation port 131, such as a cooling fluid delivered prior to, during and/or after delivery of energy by ablation element 130 (e.g. delivery of RF ablation energy). In some embodiments, system 10 can be configured to deliver fluid at a flow rate of at least 6 ml/sec, such as at least 8 ml/sec or at least 12 ml/sec during the delivery of energy by ablation element 130. Alternatively or additionally, system 10 can be configured to deliver fluid at a lower flow rate when energy is not being delivered to tissue, such as a flow rate of between 2 and 5 ml/sec when energy is not being delivered to tissue.

Hydraulic piston 155" can comprise one or more lumens, such as lumen 159 shown. Piston 155" can comprise a distal ball tip 154 and/or proximal projections 157. Hydraulic assembly 160" comprises chamber 162 which surrounds hydraulic fluid 161 (e.g. saline). Hydraulic chamber 162 can include distal projections 167. Chamber 162 slidingly receives a proximal portion of piston 155". Projections 157 engage with projections 167 within chamber 162, such as to prevent piston 155" from traveling distally from the position shown in FIG. 8A (e.g. preventing piston 155" from exiting distal end 113 of shaft 110).

Ablation catheter 100 includes ablation element 130 and mapping electrode 135, and a non-electrically conductive element, electrical isolator 132, can be positioned between ablation element 130 and mapping electrode 135. Ablation element 130 and mapping electrode 135 move in concert as hydraulic piston 155" translates relative to chamber 162, maintaining a fixed distance between ablation element 130 and mapping electrode 135. Mapping module 350 of FIG. 1 can be configured to perform bipolar calculations on signals recorded between ablation element 130 and mapping electrode 135, such as when ablation element 130 comprises an electrode. The fixed distance between the ablation element 130 and mapping electrode 135 greatly simplifies the bipolar mapping calculations performed, as described hereabove in reference to the similar components of FIGS. 7, 7A, and 7B.

In some embodiments, ablation catheter 100 comprises an articulating tip provided by articulating tip assembly 165. Articulating tip assembly 165 includes housing 166 which includes a cavity, receiving cavity 164, configured to rotatably engage a spherical member, such as ball tip 154 of piston 155". Articulating tip assembly 165 enables a distal portion of ablation catheter 100 to articulate relative to distal portion 112 of shaft 110 and piston 155". Ball tip 154 can comprise a spherical or hemispherical geometry. Cavity 164 can comprise straight and/or curved (as shown) walls, the walls configured to frictionally engage ball tip 154. The rotation angle θ of articulating tip assembly 165 can be limited by causing an interference between the proximal opening of housing 166 and piston 155" as shown in FIG. 8B.

Force maintenance assembly 150 can include sealing element 156, a component configured to prevent fluid egress out of, and/or ingress into, shaft 110 of ablation catheter 100. In some embodiments, shaft 110, projection 167, and/or projection 157 are constructed and arranged to provide a seal (e.g. without sealing element 156). In other embodiments, shaft 110, sealing element 156, projection 167, and/or projection 157 are constructed and arranged to allow hydraulic fluid 161 to exit the distal end 113 of shaft 110, such as to flush piston 155", cool mapping electrode 135 and/or neighboring tissue, lubricate piston 155", and/or reduce the hydraulic force present within force maintenance assembly 150 (as described herebelow).

Force maintenance assembly 150 can include sensing elements 158 configured to provide a signal indicative of the translation of piston 155" relative to chamber 162, such as a signal that indicates when piston 155" reaches the proximal end of chamber 162 (i.e. its maximum proximal translation). Alternatively or additionally, sensing element 158 can be configured to monitor the pressure of hydraulic fluid 161 within chamber 162. In some embodiments, sensing element 158 comprises an electrode, and hydraulic fluid 161 comprises a conductive fluid (e.g. saline), such that sensing element 158 is electrically connected to ablation element 130 and/or another electrode of articulating tip assembly 165, via an electrical pathway comprising hydraulic fluid 161 within catheter 100. A console, such as console 300 of FIG. 1, can be configured to measure the electrical properties (e.g. the impedance) of the electrical pathway between sensing element 158 and ablation element 130, and determine the distance between the two electrodes. This measurement can be used to determine the position and/or orientation of articulating tip assembly 165, such as the compression distance, as described herein. Additionally or alternatively, the measured electrical properties of the electrical pathway between the electrodes can be monitored to detect air bubbles in hydraulic fluid 161, and trigger an alert state for system 10. An alert state can comprise alerting the user to a possible safety concern, triggering cessation and/or reversal of fluid flow from the console, triggering of closure and/or blockage of irrigation ports 131, and combinations of one or more of these.

In some embodiments, ablation catheter 100 comprises a fluid pathway, chamber 163, in fluid communication with lumen 117' of shaft 110, via chamber 162 and lumen 159 of piston 155". Hydraulic fluid 161 can be provided from a console (e.g. console 300 of FIG. 1) operably attached to the proximal end and/or handle of ablation catheter 100, the hydraulic fluid 161 provided via lumen 117' to chamber 162. Chamber 162, in fluid communication with lumen 159, chamber 163, and irrigation ports 131, maintains a positive pressure, which is determined by the differential flow between lumen 117' and irrigation ports 131. In these embodiments, this positive pressure provides the hydraulic force to force maintenance assembly 150. In some embodiments, as described hereabove, hydraulic fluid 161 can exit distal end 113 of shaft 110, and the differential flow between lumen 117 and both irrigation ports 131 and distal end 113 provides the hydraulic force to force maintenance assembly 150. This differential flow can be configured (e.g. by adjusting the dimensions of irrigation port 131 and/or the gap(s) between shaft 110 and piston 155") to result in a particular ratio (e.g. a 1:1 ratio or other pre-determined ratio) of flow rate to hydraulic force (e.g. a flow rate of Xml/min correlates to a hydraulic force of Ygmf, where X and Y are known). In some embodiments, chamber 162 is in fluid communication with lumen 117', but is otherwise sealed (e.g. by the proximal end of a piston without a central lumen such as lumen 159), such that hydraulic fluid 161 remains within lumen 117' and chamber 162 (e.g. hydraulic fluid 161 does not exit catheter 100), and the hydraulic force is proportional to the pressure of hydraulic fluid 161 within chamber 162.

In some embodiments, a console (such as console 300 of FIG. 1) can be configured to provide sufficient hydraulic pressure to chamber 162 to ensure the full extension of piston 155". Additionally or alternatively, a console can be configured to provide a negative hydraulic pressure (e.g. a negative or sufficiently low pressure) to chamber 162, such as to ensure that piston 155" is fully retracted into chamber 162. In some embodiments, system 10 can be configured to perform a calibration procedure, the calibration procedure comprising providing a first hydraulic pressure to chamber 162 (e.g. the pressure required to fully extend piston 155"), and making a distance measurement between a first electrode on piston 155", such as mapping electrode 135, and a second electrode on shaft 110, such as mapping electrode 135a. The calibration further includes providing a second, different hydraulic pressure to chamber 162 (e.g. a negative or sufficiently low pressure to ensure that piston 155" is fully retracted into chamber 162), and a second distance measurement between the first and second electrodes can be made. A comparison of the two distance measurements can be performed to calibrate an electric potential field, such as is described in reference to FIG. 1 hereabove, to confirm or otherwise self-diagnose the functionality of hydraulic assembly 160" (e.g. the measured distances correlate to the fully extended and retracted positions of piston 155" or other pre-determined distance), and/or to measure or calibrate another function or component of system 10.

Referring additionally to FIG. 8B, a side sectional view of the distal portion of ablation catheter 100 of FIG. 8 is illustrated, with hydraulically actuated force maintenance assembly 150 shown in a fully compressed state, and articulating tip assembly 165 in a fully articulated state. In some embodiments, hydraulically actuated force maintenance assembly 150 is configured to compress a distance of at least 2 mm, such as at least 3 mm or at least 4 mm. In some embodiments force maintenance assembly 150 comprises and operating range between 2 mm and 5 mm, such as an operating range of approximately 2 mm, 3 mm, 4 mm or 5 mm. The operating range can comprise the full compression length of the force maintenance assembly 150, or the range can be shorter than the full compression length of the force maintenance assembly 150. In some embodiments, force maintenance assembly 150 is configured to accommodate oscillations (e.g. reciprocating motions that can include traveling from fully compressed to fully uncompressed states, due to one or more forces maintaining ablation element 130 in contact with the tissue), of at least 50 cycles per minute, at least 100 cycles per minute, at least 200 cycles per minute, at least 400 cycles per minute, at least 500 cycles per minute, or at least 600 cycles per minute.

Figure 9:
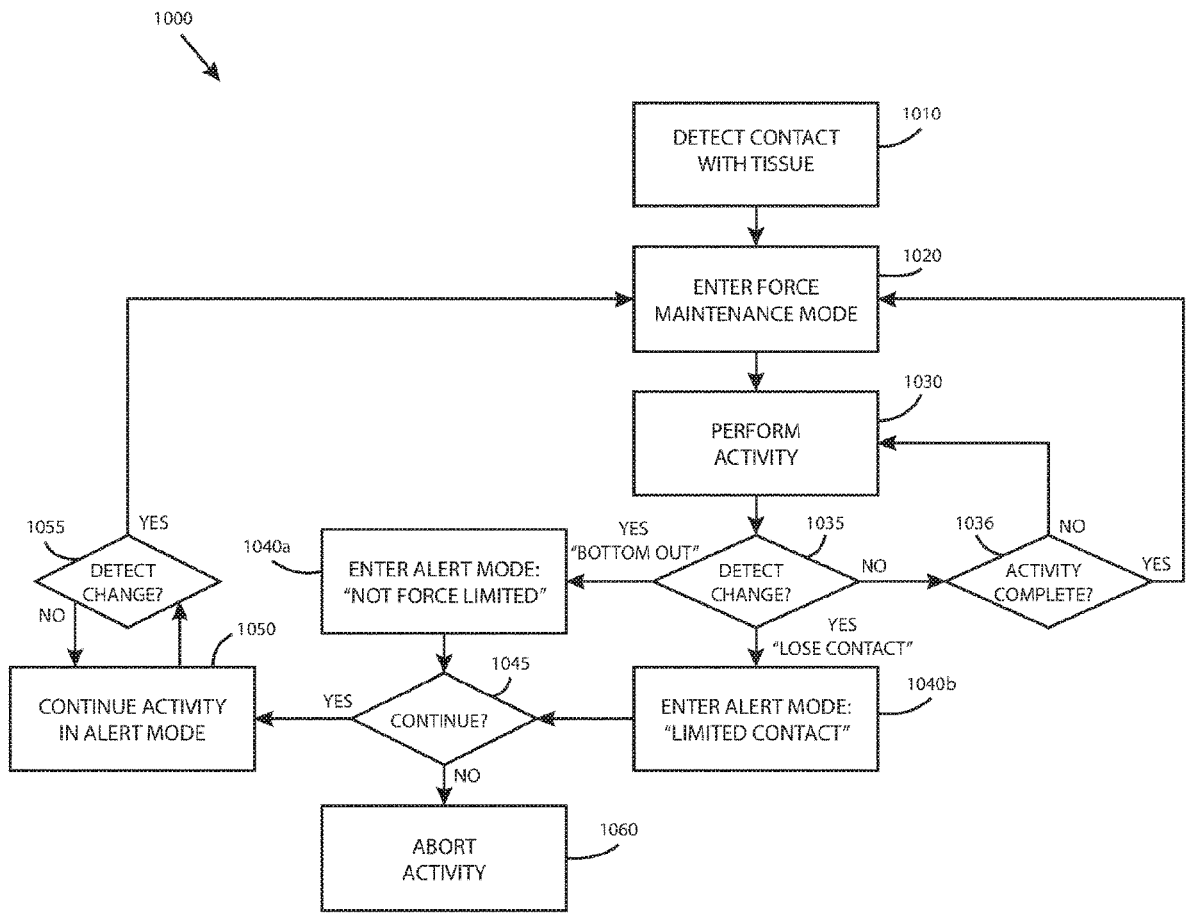
FIG. 9 illustrates a flow chart of a method for performing a medical procedure in a cardiac chamber using a force maintenance enabled catheter system, consistent with the present inventive concepts.

Referring now to FIG. 9, a flow chart of a method for performing a medical procedure in a cardiac chamber using a force maintenance enabled catheter system is illustrated, consistent with the present inventive concepts. Method 1000 comprises a series of steps of performing the medical procedure (e.g. a diagnostic procedure or a therapeutic procedure such as a tissue ablation procedure used to treat an arrhythmia), using system 10 described herein. In some embodiments, one or more steps of Method 1000 are performed automatically or semi-automatically by system 10, such as via algorithm 335 of processor 330. In STEP 1010, an ablation catheter 100 is inserted into a heart chamber of a patient and the clinician positions ablation element 130 at a desired location (e.g. in contact with a wall of the cardiac chamber). System 10 detects when ablation element 130 makes sufficient contact with cardiac tissue. In some embodiments, system 10 is configured to determine (e.g. quantify or qualify) levels of force between ablation element 130 and the cardiac tissue. The force can be measured by analyzing one or more signals recorded by one or more sensing elements or sensors of ablation catheter 100. The measured force can correlate to sufficient contact (also referred to as simply "contact" herein), when the force is above a threshold (e.g. above a threshold of zero when any measured force indicates contact). Alternatively, the threshold indicative of contact can be a force greater than zero, such as when system 10 must measure a force of at least 1 gmf, 3 gmf, 5 gmf, 7 gmf, or 10 gmf to indicate contact. Additionally or alternatively, contact can be determined by measuring changes in one or more electrical signals, for example when ablation element 130 comprises an RF ablation electrode, and system 10 detects contact by monitoring signals (e.g. tissue impedance signals) recorded via ablation element 130 and correlated to sufficient contact.

In some embodiments, system 10 is configured to determine a "contact efficiency", determined by percentage of time the ablation element 130 is in sufficient contact with the cardiac tissue, over a period of time. For example, if the ablation element 130 is intermittently in sufficient contact with the tissue for a total time of 900 ms over a period of 1000 ms, the contact efficiency during the 1000 ms window is 90%. System 10 can be configured to provide an alert, as described herein, when the contact force and/or contact efficiency is below or above a threshold. For example, over a period of time (e.g. an ablation period), contact force can be considered sufficient over the period, if either contact never falls below a threshold, or if contact efficiency is above (e.g. remains above) a threshold.

In STEP 1020, system 10 enters a force maintenance mode, wherein that ablation catheter 100 dynamically responds to motion of the cardiac wall and applies a constant or known force between ablation element 130 and tissue (e.g. when a minimum force is maintained between ablation element 130 and tissue and/or when that force is limited to a maximum value). System 10 remains in the force maintenance mode as long as contact between ablation element 130 and the cardiac tissue is maintained, and the limits of the force maintenance assembly 150 have not been exceeded, as described herebelow.

In STEP 1030, the clinician performs an activity while system 10 is in the force maintenance mode. The activity can be selected from the group consisting of: delivering energy to tissue; ablating tissue; recording electrical signals; waiting to perform a subsequent activity; and combinations of one or more of these. During STEP 1030, system 10 can monitor one or more parameters of ablation catheter 100 (e.g. via one or more sensing elements), and can be configured to detect a change in the force maintenance assembly 150, as described herein.

In STEP 1035, if no change is detected, STEP 1036 is performed in which it is determined if the activity of STEP 1030 is complete. If the activity is complete, system 10 remains in the force maintenance mode of STEP 1020, and a subsequent activity can be performed. If the activity is not complete, the clinician continues the activity in STEP 1030.

In STEP 1035, if a change in the force maintenance assembly 150 is detected, system 10 enters an alert mode of either STEP 1040a or STEP 1040b. If the travel limit of the force maintenance assembly 150 is reached, STEP 1040a is performed in which system 10 enters a "non-force limited" alert mode. Alternatively, if system 10 can no longer detect contact between ablation element 130 and the cardiac tissue, STEP 1040b is performed in which system 10 enters a "limited contact" alert mode. The limited contact alert mode of STEP 1040*b* can comprise two or more modes, for example if the measured level of contact is below a first contact threshold, but above a second contact threshold, a first alert level can indicate a "limited contact". If the measured level of contact is below the second threshold, a second alert level can indicate "lost contact". In some embodiments, the first and/or second threshold can comprise a minimum travel distance of the force maintenance element. Alternatively or additionally, the first and/or second threshold can comprise a minimum conductance measured between the ablation element and the tissue. In some embodiments, the clinician can be warned, or otherwise made aware of the alert mode, such as via haptic feedback, audible queues, visual indicators, and combinations thereof.

After STEP 1040*a* or STEP 1040*b* is performed, STEP 1045 is performed in which system 10 queries the clinician whether to continue the activity or not while in the particular alert mode. In some embodiments, for example when an alert mode has two or more alert levels, system 10 can query the clinician to continue during first level alerts, however abort the activity automatically for second level alerts. If the clinician (or system) elects to abort the activity, STEP 1060 is performed. For example, the clinician can elect to abort an ablation activity if ablation element 130 loses contact with the cardiac tissue. If the clinician elects to continue the activity, system 10 continues the activity in the alert mode, STEP 1050.

In STEP 1050, the clinician can attempt to correct the alert mode, such as by relieving pressure applied to ablation catheter 100 to restore from a non-force limited mode, or by applying additional pressure to achieve better contact and restore from a limited contact mode. If a change is detected and force maintenance is restored, STEP 1055 is performed in which system 10 enters the force maintenance mode, and the activity continues in a non-alert mode. While in STEP 1050, the clinician can elect, at any time, to abort the activity (e.g. to stop ablation of tissue). For example, if system 10 remains in a non-force limited mode for an extended period of time during an ablation activity, despite the clinician's attempts to adjust, the clinician can elect to abort the activity.

Figure 10:
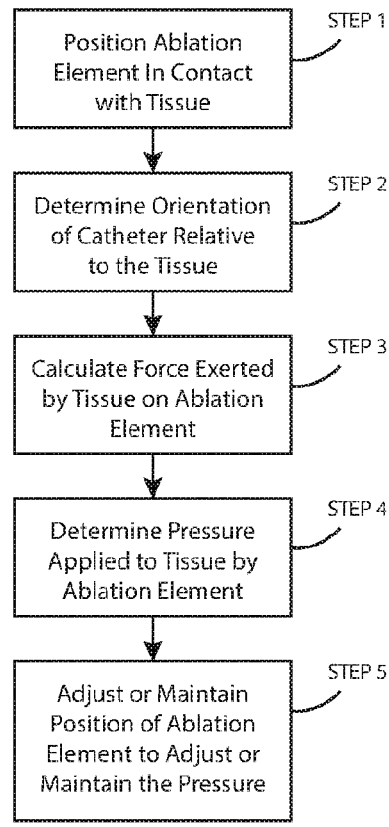
FIG. 10 illustrates a flow chart of a method for determining a contact pressure applied to tissue by the distal portion of the ablation catheter, consistent with the present inventive concepts.

FIG. 10 illustrates a flow chart of an embodiment of a method for determining a contact pressure applied to tissue by the distal portion of the ablation catheter, consistent with the present inventive concepts.

Figure 10A:
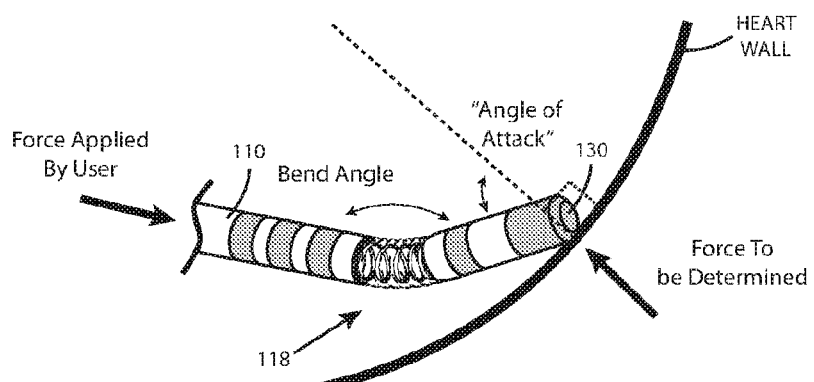
FIG. 10A illustrates a distal portion of the ablation catheter in contact with tissue to explain a method for determining pressure applied by the catheter when contacting the tissue at different angles and with different forces, consistent with the present inventive concepts.

FIG. 10A illustrates a distal portion of the ablation catheter in contact with tissue to explain a method for determining pressure applied by the catheter when contacting the tissue at different angles and with different forces, such as in FIG. 10.

Referring to FIG. 10A, a floating tip portion 118 of a catheter is brought into contact to tissue of a heart wall, in this example. A pressure exerted on the tissue by the ablation element 130 of the floating tip portion 118 of the catheter can be determined if force and area of contact are known. Contact area can be determined from orientation of the catheter relative to the tissue. The shape and size of the ablation tip are known a priori—with orientation info. The area in contact with the tissue is also known by knowing the geometry of the ablation element 130. Position and orientation of the floating tip portion 118, including "angle of attack," can be determined by an appropriately configured mapping system. The angle of attack is the angle of the floating tip portion 118 relative to an axis extending orthogonally from the surface of the tissue being treated. Any "angle of attack" determination method would work to then determine contact area and subsequently calculate pressure. A force sensor (or force sensing element) could also be used to determine the force applied to the floating tip portion 118 and/or ablation element 130. A bend angle is an angle of the floating tip portion relative to the shaft 110. Adjusting the bend angle causes an adjustment of the pressure applied by the ablation element 130 to the tissue.

With particular reference to FIG. 10, in STEP 1, the ablation element 130 is positioned within a cardiac chamber, as an example, so that it is contact with tissue (e.g. tissue of the heart wall). Contact sensing can be accomplished as described herein above. In STEP 2, an orientation of the floating tip portion 118 of the catheter relative to the tissue is determined. In STEP 3, a force exerted by the tissue on the ablation element 130 is calculated or otherwise determined. In STEP 4, a pressure applied to the tissue by the ablation element 130 is determined, based at least in part on the information from STEPSs 2 and 3. In STEP 5, the position, such as the angular position of the floating tip portion 118 relative to the tissue, is maintained or adjusted, as appropriate, to adjust or maintain the pressure of the ablation element 130 against the tissue. The desired pressure could be a discrete value or a range of acceptable pressure values.

In some embodiments, a sheath (e.g. sheath 12 described herein) could be used to help orient and/or maintain orientation of the catheter relative to the heart wall. In some embodiments, the sheath could be robotically steerable for robotic control. The sheath could help maintain normal apposition (90°) to tissue. In such a case, force maintenance could be used to only address and control axial displacement of the floating tip portion 118.

A robotically steerable sheath and/or catheter can be used to maintain and/or adjust the pressure the ablation element 130 applies to the tissue. Robotic catheter actuators can be used in conjunction with force/contact sensing elements to help maintain constant, or substantially constant, contact/force on heart wall. A feedback signal could indicate an increase or a decrease in force, or a loss of contact, and cause the robotic actuator to drive the catheter to compensate by moving the floating tip portion 118 to reestablish contact or to reestablish a desired contact pressure.

A robotic sheath and/or catheter can include actuator wires connected to solenoids in handle. Electro-active polymers can change shape or exert a load on the application of current. A catheter with electro-active polymer design could react to closed loop force sensing to maintain force on tissue. For example: two active elements could actuate or control (e.g. robotically control) lateral deflection of a catheter tip based on a sensed force.

Figure 11:
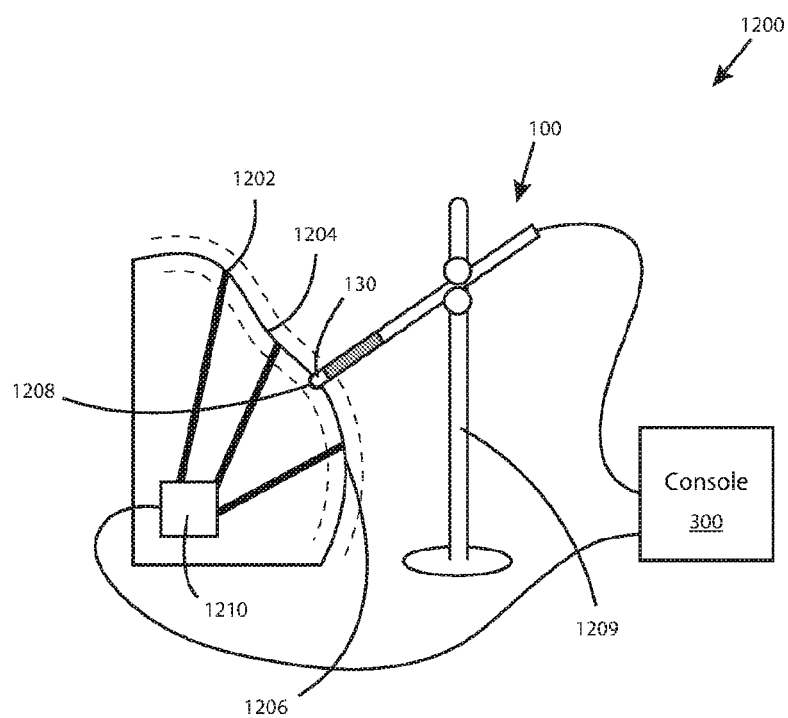
FIG. 11 illustrates an embodiment of a test fixture that can be used for determining a contact pressure applied to tissue by the distal portion of the ablation catheter, consistent with the present inventive concepts.

FIG. 11 illustrates an embodiment of a test fixture 1200 that can be used for determining a contact pressure applied to tissue by the distal portion (e.g. the ablation element 130) of the ablation catheter 100, consistent with the present inventive concepts.

Conceptually, the ablation catheters 100 and force maintenance assemblies 150 of the present inventive concepts will be used "in practice" from within a heart chamber, meaning ablation element 130 of catheter 100 will be maintaining contact with at least a concave surface of the heart chamber. However, from a motion testing standpoint (following the motion of a "wall"), a test fixture with a convex surface could be used to assess force maintenance and/or other ablation element 130 contact parameters. In the present embodiment, the test fixture 1200 has a dynamic (movable) surface, and a holder 1209 to orient a catheter 100 for testing in a fixed position relative to a testing surface of test fixture 1200. The testing surface is moved via motion assembly 1210, which is operably attached to console 300, such that motion assembly 1210 can be controlled by and/or transfer data with console 300 (to which ablation catheter 100 is also operably attached). The testing surface shown includes both concave (e.g. surface 1204) and convex (e.g. surfaces 1202 and 1206) surfaces in this embodiment. In other embodiments, the surface can include only convex or only concave surfaces.

The surface can include a feature 1208 (e.g. a divot) for "capturing" the catheter 100 tip (e.g. ablation element 130) to minimize the effects or reliance of friction during testing. For example, feature 1208 and other locations on the surface for catheter 100 tip to reside can include one or more divots, holes, dimples, ripples, and or textures that facilitate improved contact of the ablation element 130 with the testing surface. The testing surface can otherwise be configured mimic tissue's ability to deform around the ablation element 130, and have a similar pliability, softness, and/or density to the actual tissue it represents.

With reference to FIG. 1, and the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. An ablation system comprising:
    an ablation catheter comprising:
        a shaft including an irrigation lumen, a proximal end, a distal portion and a distal end;
        an ablation element configured to deliver energy to tissue; and
        a force maintenance assembly comprising a force maintenance element configured to control and/or assess contact force between the ablation element and cardiac tissue, wherein the force maintenance element comprises a piston including the ablation element, the piston extending from the shaft distal end and at least a portion of the piston translates linearly within the shaft distal portion,
        wherein the piston comprises a hydraulic piston comprising at least one irrigation port configured to allow the hydraulic fluid to exit from the irrigation lumen, and wherein the force maintenance assembly is configured to control a hydraulic fluid flow to the hydraulic piston and out of the at least one irrigation port to adjust, maintain, and control a differential hydraulic pressure that the hydraulic piston exerts on and/or against the tissue; and
    a console configured to operably attach to the ablation catheter and comprising:
        an energy delivery assembly configured to provide energy to the ablation element.

2. The ablation system according to claim 1, wherein the console is configured to control delivery of the hydraulic fluid into the piston.

3. The ablation system of claim 2, wherein the hydraulic fluid is configured to exit the ablation catheter at least one irrigation port proximate the ablation element.

4. The ablation system according to claim 1, wherein the console further comprises a force maintenance module.

5. The ablation system according to claim 4, wherein the force maintenance module is configured to adjust the force maintenance assembly.

6. The ablation system according to claim 4, wherein the force maintenance module is configured to provide a control signal to the force maintenance assembly.

7. The ablation system according to claim 4, wherein the force maintenance module is configured to operatively interact with the force maintenance assembly to control a parameter selected from the group consisting of: the fluid flow to the hydraulic piston; fluid pressure within the hydraulic piston; and combinations thereof.

8. The ablation system according to claim 1, wherein the ablation catheter further comprises at least one mapping electrode.

9. The ablation system according to claim 1, wherein the ablation catheter further comprises an articulating tip assembly.

10. The ablation system according to claim 9, wherein the articulating tip assembly comprises a spherical member and a cavity that rotatably engages the spherical member.

11. The ablation system according to claim 1, wherein the ablation catheter further comprises a contact sensor configured to produce a signal representative of the amount of contact between the ablation element and tissue.

12. The ablation system according to claim 1, wherein the energy delivered by the ablation element comprises energy selected from the group consisting of: thermal energy; heat energy; cryogenic energy; electromagnetic energy; radio frequency (RF) energy; microwave energy; light energy; light energy provided by a laser; sound energy; subsonic energy; ultrasound energy; chemical energy; and combinations thereof.

13. The ablation system according to claim 1, wherein the energy delivered by the ablation element comprises at least two forms of energy selected from the group consisting of: electromagnetic energy; RF energy; microwave energy; light energy; laser light energy; cryogenic energy; ultrasound energy; and combinations thereof.

14. The ablation system according to claim 1, wherein the force maintenance assembly is configured to dynamically respond to movement of a heart wall.

15. The ablation system according to claim 1, wherein the force maintenance assembly is configured to compress up to a maximum compression distance, and wherein the maximum compression distance comprises a distance between 0.1 mm and 10 mm.

16. The ablation system according to claim 1, further comprising a locking element configured to lock the force maintenance assembly to prevent linear and/or angular movement of the ablation element with respect to the shaft.

17. The ablation system according to claim 1, wherein the force maintenance assembly further comprises at least one displacement sensor configured to produce a signal correlating to a travel distance of the force maintenance assembly.

18. The ablation system according to claim 17, wherein the system is configured to determine when the travel distance is equal to a maximum compression distance based on the sensor signal.

* * * * *